(12) United States Patent
Ito

(10) Patent No.: US 7,306,533 B2
(45) Date of Patent: Dec. 11, 2007

(54) LIGHT SOURCE APPARATUS FOR ELECTRONIC ENDOSCOPE AND ELECTRONIC ENDOSCOPE

(75) Inventor: Shunichi Ito, Tokyo (JP)

(73) Assignee: PENTAX Corporation, Tokyo (JP)

( * ) Notice: Subject to any disclaimer, the term of this patent is extended or adjusted under 35 U.S.C. 154(b) by 307 days.

(21) Appl. No.: 11/219,825

(22) Filed: Sep. 7, 2005

(65) Prior Publication Data

US 2006/0052214 A1 Mar. 9, 2006

(30) Foreign Application Priority Data

Sep. 8, 2004 (JP) ............................. 2004-261363
Feb. 2, 2005 (JP) ............................. 2005-026568

(51) Int. Cl.
*F16H 3/72* (2006.01)
(52) U.S. Cl. .................... 475/5; 362/574; 600/178; 475/282; 475/311; 475/317; 180/65.2
(58) Field of Classification Search ..................... None
See application file for complete search history.

(56) References Cited

U.S. PATENT DOCUMENTS

| 4,729,018 | A * | 3/1988 | Watanabe et al. | ............. | 348/69 |
| 6,413,211 | B2 * | 7/2002 | Higuchi et al. | ............. | 600/181 |
| 6,929,605 | B2 | 8/2005 | Kurosawa | | |
| 6,974,240 | B2 * | 12/2005 | Takahashi | .................. | 362/574 |

| 2004/0209722 | A1 * | 10/2004 | Ai | ................................ | 475/5 |
| 2004/0210112 | A1 | 10/2004 | Ota | | |
| 2005/0220447 | A1 | 10/2005 | Ito | | |

FOREIGN PATENT DOCUMENTS

| JP | 62-69222 | 3/1987 |
| JP | 7-85132 | 9/1995 |
| JP | 3370871 | 11/2002 |
| JP | 2004-103941 | 4/2004 |

OTHER PUBLICATIONS

U.S. Appl. No. 11/256,075 to Ito, which was filed Oct. 24, 2005.

* cited by examiner

*Primary Examiner*—David D. Le
(74) *Attorney, Agent, or Firm*—Greenblum & Bernstein, P.L.C.

(57) ABSTRACT

A light source apparatus for an electronic endoscope includes a light source; a rotary shutter having a pair of aperture controlling rotary plates; a first planetary gear mechanism including a first internal tooth gear, a first sun gear, and a first planet gear; a second planetary gear mechanism including a second internal tooth gear, a second sun gear, and a second planet gear; and carriers holding the first and second planet gears in a same phase position and supporting the first and second planet gears. One of the first sun gear and the first internal tooth gear is non-rotatably fixed, and the other thereof is rotated together with one of the aperture controlling rotary plates, and one of the second sun gear and the second internal tooth gear of the second planetary gear mechanism is driven together with the other thereof by a phase difference motor.

14 Claims, 21 Drawing Sheets

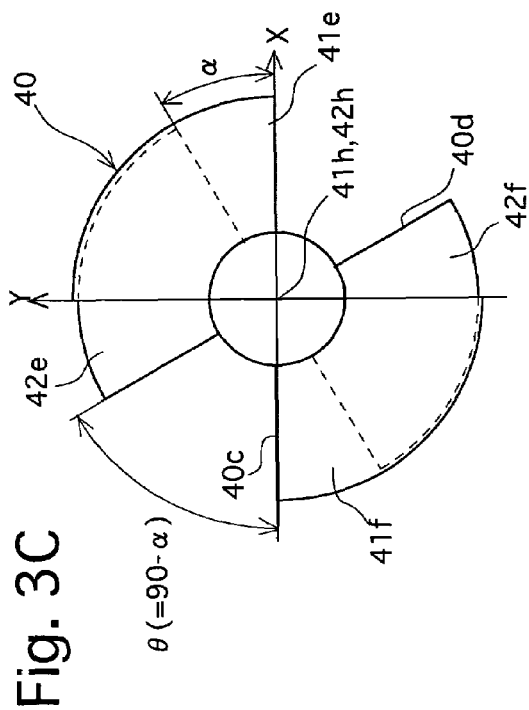
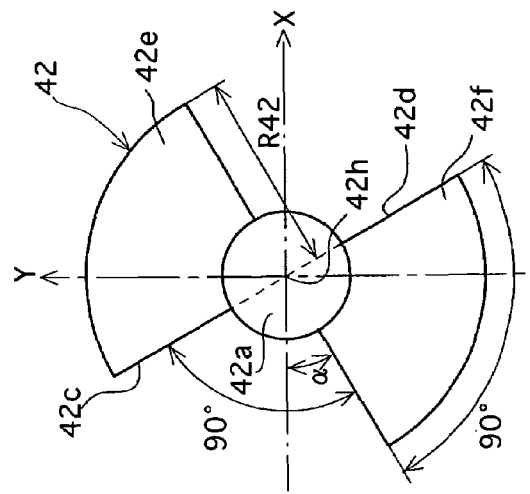
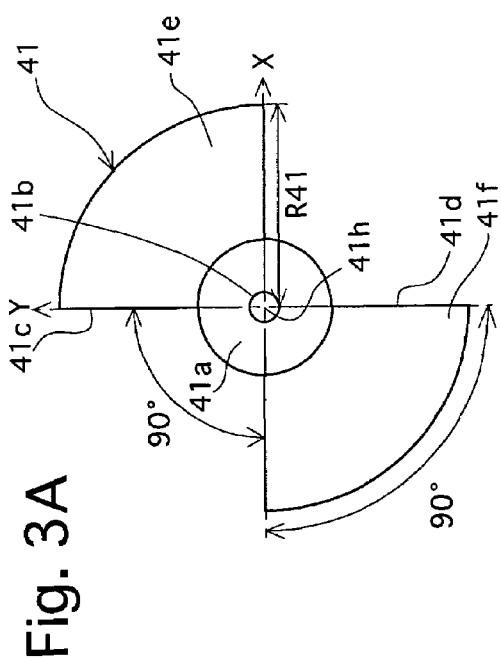
Fig. 3A
Fig. 3B
Fig. 3C

LIGHT SOURCE APPARATUS FOR ELECTRONIC ENDOSCOPE AND ELECTRONIC ENDOSCOPE

BACKGROUND OF THE INVENTION

1. Field of the Invention

The present invention relates to a light source apparatus for an electronic endoscope using a plurality of aperture-controlling rotary plates, and an electronic endoscope.

2. Description of the Prior Art

In a conventional electronic endoscope, in order to provide appropriate light modulation, an endoscope record apparatus has been proposed in, for example, Japanese Unexamined Patent Publication No. 62-69222. The apparatus disclosed in this publication is provided with a rotary shutter having a rotatable shaft, wherein the distance between the rotatable shaft and the axis of illumination light emitted from a light source for the endoscope is variable. The rotary shutter is shaped so that a difference in the peripheral speed occurs between the radial portions thereof or the aperture is varied in accordance with the rotation of the rotary shutter. The light modulation is carried out due to a change in the distance between the axes using the peripheral speed difference.

In Japanese Unexamined Patent Publication No. 62-69222, light modulation can be performed, however, the structure of the rotary shutter is complex. Furthermore, it is necessary to provide a mechanism to vary the distance between the rotary shutter and the optical axis of the light source for the endoscope. Accordingly, the manufacturing cost is high and the manufacturing process is troublesome. Moreover, in order to achieve such a construction, the outer diameter of the rotary shutter must be several times larger than that of the light bundle, thus resulting in an increase in the size of the rotary shutter. If the rotary shutter is asymmetrical in shape with respect to the rotation axis thereof in order to vary the aperture, the center of rotation does not align with the center of gravity, so that the rotary shutter tends to lose balance during rotation. Consequently, correct emission of the illumination light cannot take place and the rotary shutter and the surrounding members may break.

In view of the problems discussed above, the assignee of the present application has proposed a light source apparatus for an electronic endoscope having a light source and a rotary shutter whose rotation axis extends parallel with the optical axis of the light source and which intercepts or emits illumination light emitted from the light source toward a light guide. The rotary shutter is provided with a pair of aperture controlling rotary plates coaxial with each other, which are rotatable together and which are each provided with light intercepting portions and opening portions arranged alternately in the rotation direction, whereby the opening angle of the opening portions of the rotary shutter as a whole is varied by relatively rotating the aperture controlling rotary plates to thereby control the quantity of light to be emitted (Japanese Patent Application No. 2004-103941).

In the invention disclosed in Japanese patent Application No. 2004-103941, two motors are used to rotate the pair of aperture controlling rotary plates. One of the motors is stationary and the other motor rotates together with the aperture controlling rotary plate, and hence, providing a countermeasure to prevent interference of harnesses (wirings) extending from the motors.

Furthermore, if smooth rotation of the aperture controlling rotary plates does not occur for some reason, the illumination light may unintentionally flicker. If the opening area defined between the pair of aperture controlling rotary plates is large (if the brightness is high), the rotary shutter is less affected by the flickering of the illumination light (variation of brightness). However, if the opening area is small (if the brightness is low), the brightness of the illumination light is largely deviated from a desired value, and accordingly, the affection by the flickering of the illumination light is not negligible.

Moreover, if smooth rotation of the aperture controlling rotary plates does not occur, the rotation speed of the aperture controlling rotary plates (shutter speed) cannot be increased much.

SUMMARY OF THE INVENTION

The present invention provides a light source apparatus for an electronic endoscope and an electronic endoscope, in which no countermeasure to interference of the harnesses is necessary, and a smooth rotation of the pair of aperture controlling rotary plates can be achieved.

According to an aspect of the present invention, a light source apparatus for an electronic endoscope is provided, including a light source; a rotary shutter having a rotation axis extending parallel with the optical axis of the light source, for one of intercepting and emitting illumination light emitted from the light source toward a light guide, the rotary shutter being provided with a pair of aperture controlling rotary plates, coaxial with each other, which are selectively capable of rotating one of relative to and together with each other, and which are each provided with light interception portions and opening portions alternately arranged in the rotation direction, wherein the combined opening angle of the opening portions of the rotary shutter is varied by a relative rotation of the pair of aperture controlling rotary plates, and wherein the amount of the light emitted is controlled by integral rotation of the pair of aperture controlling rotary plates; a first planetary gear mechanism including a first internal tooth gear which is provided coaxial with the rotation axis of the rotary shutter, a first sun gear coaxial with an axis of the first internal tooth gear, and a first planet gear which simultaneously engages with the first internal tooth gear and the first sun gear; a second planetary gear mechanism including a second internal tooth gear identical to the first internal tooth gear and coaxial with the rotation axis of the rotary shutter, a second sun gear identical to the first sun gear and coaxial with an axis of the second internal tooth gear, and a second planet gear identical to the first planet gear and which simultaneously engages with the second internal tooth gear and the second sun gear; and a carrier mechanism which holds the first and second planet gears in a same phase position, with respect to the first and second internal tooth gears, and supports the first and second planet gears so as to relatively rotate. One of the first sun gear and the first internal tooth gear of the first planetary gear mechanism is non-rotatably fixed, and the other of the first sun gear and the first internal tooth gear is rotated together with one of the aperture controlling rotary plates by a motor, and one of the second sun gear and the second internal tooth gear of the second planetary gear mechanism is driven together with the other of the aperture controlling rotary plates by a phase difference motor.

It is desirable for the carrier mechanism to include a pair of carrier plates which are rotatable about an axis coincident with the rotation axis of the rotary shutter, wherein one and the other of the pair of carrier plates supports a pair of the first planet gears and a pair of the second planet gears at the both ends thereof, respectively.

It is desirable for the first internal tooth gear to be fixed so as not to rotate. The motor drives the first sun gear and one of the aperture controlling rotary plates. The phase difference motor drives the second internal tooth gear.

It is desirable for the second internal tooth gear to be rotatably supported by a gear bearing.

In an embodiment, a light source apparatus for an electronic endoscope is provided, including a light source; a rotary shutter having a rotation axis extending parallel with the optical axis of the light source, for one of intercepting and emitting illumination light emitted from the light source toward a light guide, the rotary shutter being provided with a pair of aperture controlling rotary plates, coaxial with each other, which are selectively capable of rotating one of relative to and together with each other, and which are each provided with light interception portions and opening portions alternately arranged in the rotation direction, wherein the combined opening angle of the opening portions of the rotary shutter is varied by a relative rotation of the pair of aperture controlling rotary plates, and wherein the amount of the light emitted is controlled by integral rotation of the aperture controlling rotary plates; a first planetary gear mechanism including a first internal tooth gear which is provided coaxial with the rotation axis of the rotary shutter, a first sun gear coaxial with an axis of the first internal tooth gear, and a first planet gear which simultaneously engages with the first internal tooth gear and the first sun gear; a second planetary gear mechanism including a second internal tooth gear identical to the first internal tooth gear and coaxial with the rotation axis of the rotary shutter, a second sun gear identical to the first sun gear and coaxial with an axis of the second internal tooth gear, and a second planet gear identical to the first planet gear and which simultaneously engages with the second internal tooth gear and the second sun gear; and a carrier mechanism which holds the first and second planet gears in a same phase position, with respect to the first and second internal tooth gears, and supports the first and second planet gears so as to relatively rotate. The second internal tooth gear is fixed so as no to rotate, the second sun gear and one of the aperture controlling rotary plates are rotated together, the first sun gear and the other of the aperture controlling rotary plates are driven by a motor, and the first internal tooth gear is driven by a phase difference motor.

It is desirable for the carrier mechanism to include a pair of carrier plates which are rotatable about an axis coincident with the rotation axis of the rotary shutter, wherein one and the other of the pair of carrier plates supports a pair of the first planet gears and a pair of the second planet gears at the both ends thereof, respectively.

It is desirable for the first internal tooth gear to be rotatably supported by a gear bearing.

It is desirable for the second sun gear and the other of the aperture controlling rotary plates to be made integral via a first support member. The one of the aperture controlling rotary plates is fixed to a second support member which is rotated by the motor. A rotation-center projection provided on the second support member is relatively rotatably fitted in a support hole formed in the first support member. An annular support member which is in contact with the support hole and the center projection is inserted in an annular clearance defined between the support hole and the center projection.

It is desirable for the second sun gear and the other of the aperture controlling rotary plates to be made integral via a first support member. The one of the aperture controlling rotary plates is connected to a second support member which is rotated by the motor. A rotation-center projection provided on the second support member is relatively rotatably fitted in a support hole formed in the first support member. A plurality of arc-shaped support members, which are in contact with the support hole and a biasing device for biasing each arc-shaped support member toward the support hole, are inserted in an annular clearance defined between the support hole and the rotation-center projection.

It is desirable for the first sun gear to be fixed so as not to rotate, wherein the first internal tooth gear is secured to the one of the aperture controlling rotary plates and is driven by the motor, the second internal tooth gear is secured to the other of the aperture controlling rotary plates, and the second sun gear is driven by a phase difference motor.

It is desirable for one of the first and second internal tooth gears to be rotatably supported by a gear bearing.

The light source apparatus can include carrier bearings fitted in center holes formed in the carriers to relatively rotatably support the carriers.

It is desirable for at least one of the first and second planet gears to be made of a thermoplastic elastomer and to be in the form of a profile shifted gear shifted in a positive direction with respect to a standard gear having the same number of teeth and the same module.

The electronic endoscope can include an operating portion; an insertion portion extending from the operating portion and inserted into an object to be viewed; and a light guide which is inserted in the operating portion and the insertion portion, the light guide including a distal end extending to a distal end of the insertion portion. The light source emits illumination light to the light guide. According to the present invention, a light source apparatus for an electronic endoscope, and an electronic endoscope, can be provided in which the components of the planetary gear mechanisms constituting carriers can be smoothly operated, flickering of the illumination light, leading to a variation in brightness, does not occur, and the shutter can be actuated at high speed.

The present disclosure relates to subject matter contained in Japanese Patent Application No. 2004-261363 (filed on Sep. 8, 2004) and in Japanese Patent Application No. 2005-26568 (filed on Feb. 2, 2005) which are expressly incorporated herein in their entireties.

BRIEF DESCRIPTION OF THE DRAWINGS

The present invention will be discussed below in detail with reference to the accompanying drawings, in which:

FIG. 3A is a front elevational view of a first aperture controlling rotary plate;

FIG. 3B is a front elevational view of a second aperture controlling rotary plate;

FIG. 3C is a front elevational view of a rotary shutter;

DESCRIPTION OF THE PREFERRED EMBODIMENTS

A first embodiment of the present invention will be discussed below with reference to FIGS. 1 through 5.

Figure 1:
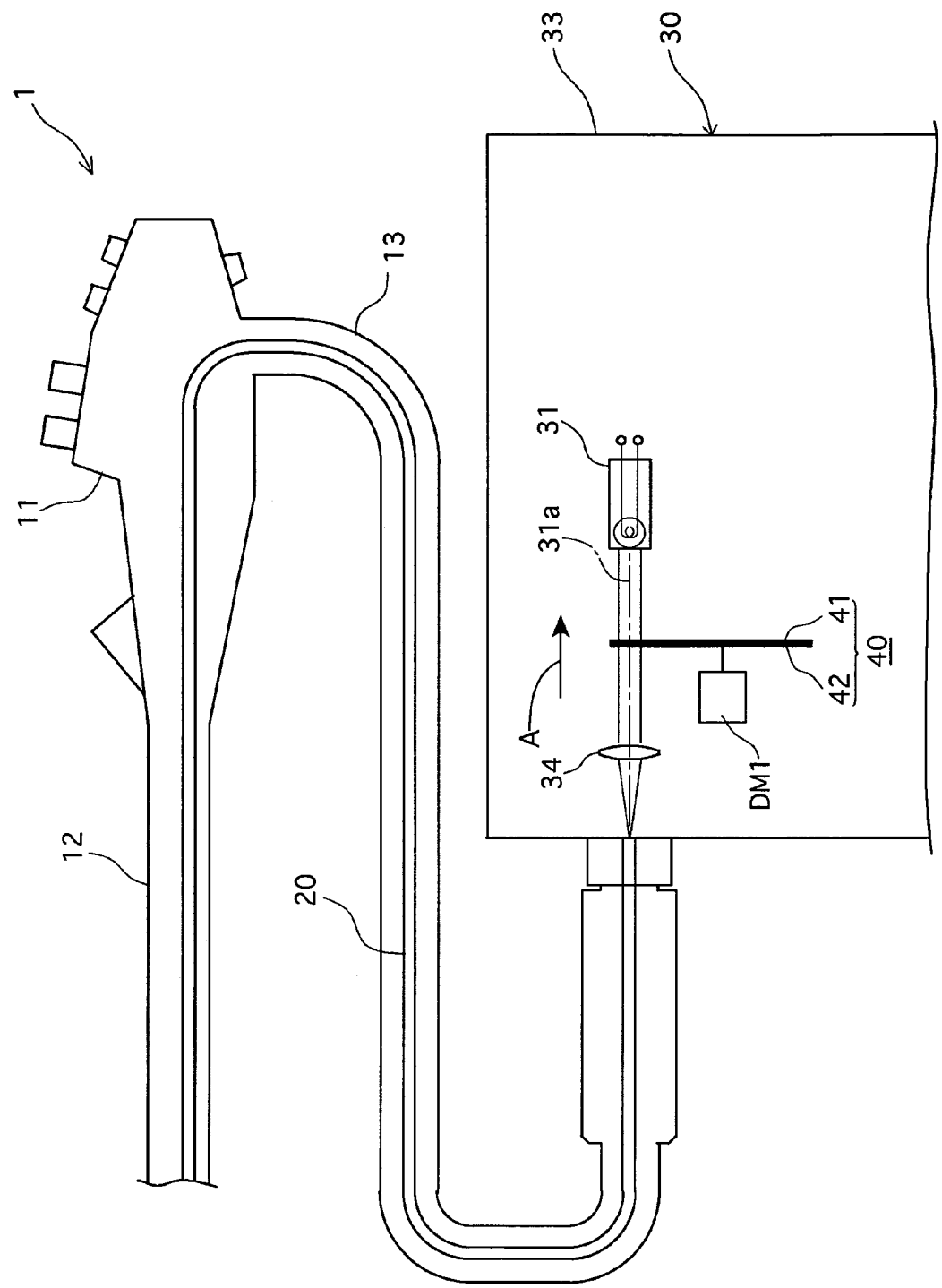
FIG. 1 is a schematic view of an internal structure of an electronic endoscope according to a first embodiment of the present invention.

As can be seen in FIG. 1, an electronic endoscope 1 includes an operating portion 11 which is held by an operator, a flexible and elongated insertion portion 12 extending from the operating portion, and a connecting tube 13 which extends from the insertion portion 12. A light guide (light guide fiber) 20 is provided in the operating portion 11, the insertion portion 12, and the connecting tube 13 to emit illumination light out of an emitting end surface formed at the distal end of the endoscope 1.

Figure 2:
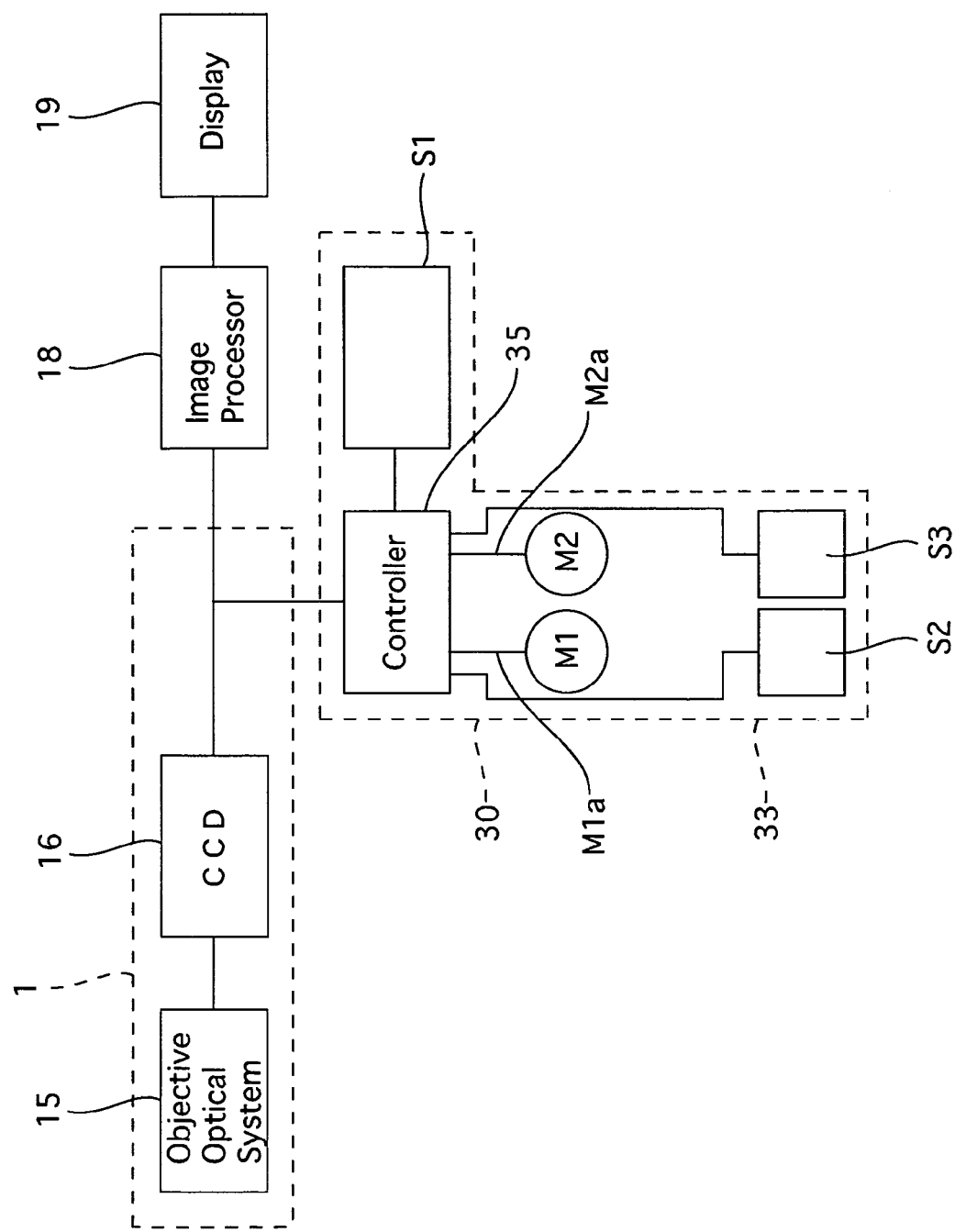
FIG. 2 is a block diagram of an electronic endoscope.

The electronic endoscope 1 is connected to a light source apparatus 30 through the connecting tube 13. The light source apparatus 30 is provided with a housing 33 in which a lamp (light source) 31 is provided. Illumination light emitted from the lamp 31 is incident upon the light guide 20 at the incident end surface thereof. The light transmitted through the light guide 20 is emitted to the outside of the electronic endoscope from the distal end of the insertion portion 12. Light reflected by a viewed object is incident upon the insertion portion 12 through an objective optical system 15 provided at the distal end of the insertion portion 12 and is accumulated as electric charges in a CCD (solid image pickup device) 16 (FIG. 2). All the image pixel data of the CCD 16 is processed by an image processing circuit 18, so that an image is displayed in a display 19, based on the image pixel data.

The light source apparatus 30 includes, in addition to the lamp 31, a rotary shutter 40 which functions as a light controller for controlling or intercepting illumination light emitted from the lamp 31 (having an optical axis 31a), a condenser lens 34 which condenses the light emitted from the lamp 31 and guides the light to an incident end surface of a light guide 20, and a drive mechanism DM1 for driving the rotary shutter 40.

As shown in FIGS. 3A, 3B and 3C, the rotary shutter 40 is provided with a first aperture controlling rotary plate 41 and a second aperture controlling rotary plate 42 which have substantially the same outer shape.

The first aperture controlling plate 41 shown in FIG. 3A is an aluminum flat plate provided perpendicular to the optical axis 31a and includes a circular center portion 41a and a pair of light intercepting portions 41e and 41f, connected to the central portion 41a. The central portion 41a is provided with a circular center hole 41b located at a center axis 41h of the central portion 41a. The light intercepting portions 41e and 41f are arranged symmetrically with respect to the center axis 41h of the central portion 41a and are each substantially in the form of a sector having a central angle of 90 degrees which is centered on the center axis 41h. Opening portions 41c and 41d having an angle of 90 degrees with respect to the center axis 41h are formed between the light intercepting portions 41e and 41f. As shown in FIG. 3A, the linear distance (radius of the first aperture controlling rotary plate 41) between the center axis 41h and the outer peripheries of the light intercepting portions 41e and 41f is R41.

The second aperture controlling plate 42 shown in FIG. 3B is aluminum flat plate provided perpendicular to the optical axis 31a and includes a circular disc portion 42a and a pair of light intercepting portions 42e and 42f. The light intercepting portions 42e and 42f are arranged symmetrically with respect to the center axis 42h of the central disc portion 42a and are each substantially in the form of a sector having a central angle of 90 degrees which is centered on the center axis 42h. Opening portions 42c and 42d, each having an angle of 90 degrees with respect to the center axis 42h, are formed between the light intercepting portions 42e and 42f. As shown in FIG. 3B, the linear distance (radius of the second aperture controlling rotary plate 42) between the center axis 42h and the outer peripheries of the light intercepting portions 42e and 42f is R42 (<R41).

The radii R41 and R42 are determined to be equal to or larger than the diameter of the light bundle emitted from the lamp 31 and made incident upon the rotary shutter 40. Provided that this requirement is met, R41 can be equal to or smaller than R42 (R41=R42 or R41<R42). In the first and second aperture controlling rotary plates 41 and 42 in the illustrated embodiment, although the opening portions and the light intercepting portions have a center angle of 90 degrees with respect to the respective center axes 41h and

42h, the center angle may be other than 90 degrees and the first and second aperture controlling rotary plates 41 and 42 may be different in shape.

As shown in FIG. 3C, the center axes 41h and 42h of the first and second aperture controlling rotary plates 41 and 42 concur with each other (align each other), and the first aperture controlling rotary plate 41 is arranged so that the light intercepting portions 41e and 41f are located within the first quadrant and the third quadrant in X-Y coordinates (abscissa X and ordinate Y), respectively. The second aperture controlling rotary plate 42 is arranged so that the light intercepting portions 42e and 42f are deviated by an angle α in the counterclockwise direction with respect to the light intercepting portions 41e and 41f, respectively. This deviation direction of the rotary plate is determined based on the direction in which the lamp 31 is viewed from the condenser lens 34 side (see arrow "A" in FIGS. 1 and 4), and the same is true in the second and third embodiments discussed hereinafter (see arrow "A" in FIGS. 6, 12, 15, 19 and 21). Consequently, the opening portions 41c and 41d are partly covered by the light intercepting portions 42e and 42f, respectively. The opening portions 40c and 40d of the rotary shutter 40 thus obtained are substantially in the form of sectors which are arranged symmetrically with respect to the center axes 41h and 42h and which have a center angle (opening angle) θ equal to 90−α. The opening angle θ can be varied between a range of 0 (smallest angle) to 90 degrees (largest angle) by relatively rotating the first and second aperture controlling rotary plates 41 and 42.

The drive mechanism DM1 will be explained below with reference to FIGS. 4 and 5.

The drive shaft (rotating shaft) 50 which extends perpendicularly to the first and second aperture controlling rotary plates 41 and 42 (i.e., parallel with the optical axis 31a) relatively rotatably extends through the center hole 41b formed in the first aperture controlling rotary plate 41 (the center axes 41h and 42h are coaxial with the drive shaft 50 and an extension of the drive shaft 50). The drive shaft 50 is secured at one end thereof to the second aperture controlling rotary plate 42 at the center axis 42h. The other end of the drive shaft 50 is coaxially connected (i.e., "coaxial" when viewed from the direction of an arrow "A") to a drive shaft of a chopper motor M1 secured to the casing 33 of the light source apparatus 30. When the chopper motor M1 is driven, the drive shaft 50 is rotated about its axis. An internal tooth gear (first internal tooth gear) 51 in the form of a ring coaxial with the drive shaft 50 is provided around the drive shaft 50 and is secured to the housing 33 of the light source apparatus 30. The internal tooth gear 51 is hatched in FIG. 4 to indicate that the internal tooth gear is a stationary member. The internal tooth gear 51 is provided on its entire inner peripheral surface, with sixty internal teeth 52 at equal pitches. The detailed shape of the internal teeth 52 (and all the other gears shown in FIG. 4 discussed hereinafter) is not shown for simplicity. The drive shaft 50 extends through a center portion of a first circular sun gear 53 which is smaller in diameter than the internal tooth gear 51 and which lies in the same plane as the internal tooth gear 51. The first sun gear 53 is coaxially secured to the drive shaft 50. The first sun gear 53 is provided, on its entire outer peripheral surface, with twenty four external teeth 54 at equal pitches. Two first planet gears 55 are provided between the internal tooth gear 51 and the first sun gear 53. The planet gears 55 are each provided with eighteen external teeth at equal pitches. The planet gears 55 are identical in diameter to the first sun gear 53 and are arranged symmetrically with respect to the first sun gear 53. The external teeth 56 of the first planet gears 55 are in mesh with the internal teeth 52 of the internal tooth gear 51 and the external teeth 54 of the first sun gear 53. The planet gears 55 are each provided with a circular mount hole 55a at the central portion thereof, so that the end portions of driven shafts 57 that are located adjacent to the chopper motor M1 and extend in parallel with the drive shaft 50 are fitted and secured in the mount holes 55a. A first carrier (carrier plate) 58 is provided between the chopper motor M1 and the internal tooth gear 51, the first sun gear 53 and the first planet gears 55. The first carrier 58 extends in the radial direction of the internal tooth gear 51. The first carrier 58 is provided, on its center portion (rotation center), with a circular hole 59 through which the drive shaft 50 extends so as to relatively rotate. The first carrier 58 is provided on its opposite ends with engagement holes 60 in which the ends of the driven shafts 57 adjacent to the chopper motor M1 are inserted so as to relatively rotate.

The internal tooth gear 51, the first sun gear 53 and the first planet gears 55 constitute a first planetary gear mechanism GM1.

The ends of the driven shafts 57 on the first aperture controlling rotary plate 41 side relatively rotatably fitted in engagement holes 62 formed in opposite ends of a second carrier (carrier plate) 61 identical in shape to the first carrier 58. The second carrier 61 is provided on its center axis (rotation center) with a circular mount hole (rotation center hole) 63 in which a rotary cylinder (carrier bearing) 64, which is rotatable relative to the drive shaft 50, extends coaxially with the drive shaft 50. The rotary cylinder 64 is mounted on the end of the drive shaft 50 adjacent to the first aperture controlling rotary plate 41. The end of the rotary cylinder 64 on the chopper motor M1 side is coaxially secured to the center portion of the second sun gear 66 coaxial with the first sun gear 53. The second sun gear 66 is identical in diameter to the first sun gear 53 and is provided with external teeth identical to those of the first sun gear 53. The drive shaft 50 extends through the center hole 67 of the second sun gear 66. The end of the rotary cylinder 64 which is adjacent to the second aperture controlling rotary plate 42 is fitted in and secured to the center hole 41b of the first aperture controlling rotary plate 41, so that the inner space of the rotary cylinder 64 is communicatively connected with the center hole 41b. An internal/external tooth gear (second internal tooth gear) 68 coaxial with the second sun gear 66 is provided around the second sun gear 66 and is rotatable about the drive shaft 50. The second internal tooth gear 68 lies in the same plane as the second sun gear 66. The second internal tooth gear 68 is provided on its inner peripheral surface with internal teeth 69 identical to those of the internal tooth gear 51. Furthermore, two second planet gears 70 are provided between the internal/external tooth gear 68 and the second sun gear 66. The planet gears 70 are each provided with external teeth 71 identical to those of the first planet gears 55. The planet gears 70 are identical in diameter to the first planet gears 55 and are arranged symmetrically with respect to the second sun gear 66. The driven shafts 57 are rotatably fitted in the center holes 70a of the second internal tooth gears 70. The external teeth 71 of the second planet gears 70 are in mesh with the internal teeth 69 of the internal/external tooth gear 68 and the external teeth 65 of the second sun gear 66. The internal/external tooth gear 68 is provided, on its entire outer peripheral surface, with a large number of external teeth 72 at equal pitches. The external teeth 72 are in mesh with external teeth 74 formed on the entire outer peripheral surface of a drive gear 73 at equal pitches. The drive gear 73 is rotated about a rotation shaft 75 thereof by a phase difference motor M2 secured to the casing 33 of the light source apparatus 30.

The internal/external tooth gear 68, the second sun gear 66 and the second planet gears 70 constitute the second planetary gear mechanism GM2. The first and second carriers 58 and 61 constitute a carrier mechanism which holds the first and second planet gears 55 and 70 in a same phase position.

As shown in FIG. 2, the harnesses (wiring) M1a and M2a extend from the body of the chopper motor M1 and the body of the phase difference motor M2 and are connected to a controller (control device) 35 which includes a CPU (central processing unit) incorporated in the light source apparatus 30. The controller 35 controls the chopper motor M1 and the phase difference motor M2 and calculates the brightness of the object based on the brightness signal supplied from the CCD 16. The light source apparatus 30 is provided therein with an automatic light control switch S1, a chopper motor control button S2 and a phase difference motor control button S3, which are respectively connected to the controller 35.

The operation of the drive mechanism DM1 and the rotary shutter 40 will be discussed below mainly with reference to FIGS. 4 and 5.

When the chopper motor M1 is rotated in the clockwise direction, the drive shaft 50 and the first sun gear 53 are rotated in the clockwise direction at the rotation speed SP1. Consequently, the two first planet gears 55 are rotated about the driven shafts 57 in the counterclockwise direction and revolve around the drive shaft 50 in the clockwise direction. The second carrier 61 which is synchronized with the first carrier 58 through the driven shafts 57 (i.e., the second carrier 61 is always located at the same phase position as the first carrier 58 with respect to the internal tooth gear 51 and the internal/external tooth gear 68) is rotated in the clockwise direction, so that the two second planet gears 70 rotate about the driven shafts 57 in the counterclockwise direction and revolve about the drive shaft 50 in the clockwise direction. The rotation speed and revolution speed of the second planet gears 70 are the same as those of the first planet gears 55. Therefore, the second sun gear 66 is rotated in the clockwise direction at the speed SP1.

As can be understood from the foregoing, the second sun gear 66 obtains the same rotation speed SP1 as the first sun gear 53 from the chopper motor M1. However, in practice, the second sun gear 66 is rotated at a speed different from SP1 because the drive force of the phase difference motor M2 is also transmitted to the second sun gear 66.

Namely, when the phase difference motor M2 rotates in the direction opposite to the chopper motor M1 to rotate the internal/external tooth gear 68 in the clockwise direction, the rotational force of the internal/external tooth gear 68 is transmitted to the second planet gears 70, so that the revolving speed of the second planet gears 70 in the counterclockwise direction is larger than that when the second planet gears 70 are driven only by the drive force of the chopper motor M1. Therefore, the second sun gear 66 in mesh with the second planet gears 70 is rotated in the clockwise direction at a rotation speed SP2 higher than the rotation speed SP1 of the first sun gear 53.

When the phase difference motor M2 is rotated in the same direction as the chopper motor M1 (i.e., the clockwise direction), the internal/external tooth gear 68 is rotated in the counterclockwise direction, so that the revolving speed of the second planet gears 70 in the counterclockwise direction is smaller than when the second planet gears 70 are driven only by the chopper motor M1. Consequently, the rotation speed SP3 of the second sun gear 66 in the clockwise direction is smaller than SP1.

When there is a difference between the rotation speed SP2 (SP3) of the second sun gear 66 and the rotation speed SP1 of the first sun gear 53, a difference in the rotation speed is caused between the first aperture controlling rotary plate 41 and the second aperture controlling rotary plate 42 and, accordingly, the center angles θ of the opening portions 40c and 40d gradually vary in the range of 0 to 90 degrees.

Automatic and manual light control using the drive mechanism DM1 can be carried out in the light source apparatus 30. When the automatic light control and the manual light control are carried out, the insertion portion 12 of the electronic endoscope 1 is inserted in the patient's body (viewed object) and the viewed site is illuminated with the illumination light emitted from the lamp 31 wherein the controller 35 constantly detects the brightness of the viewed site based on the brightness signal supplied from the CCD 16.

When the automatic light control switch S1 is turned ON, the controller 35 which receives a command from the automatic light control switch S1 automatically controls the rotation direction and rotation speed of the chopper motor M1 and the phase difference motor M2 in accordance with the brightness signal from the CCD 16 to vary the opening angles θ of the opening portions 40c and 40d in the range of 0 to 90 degrees. Consequently, the quantity of illumination light transmitted through the rotary shutter 40 is varied so that the brightness of the viewed site is always at a desired value.

In the manual light control, the automatic light control switch S1 is turned OFF and the chopper motor control button S2 and the phase difference motor control button S3 are manually operated.

First, the chopper motor M1 and the phase difference motor M2 are rotated by actuating the chopper motor control button S2 and the phase difference control button S3. When the opening angle θ of the opening portions 40c and 40d becomes a desired value, the phase difference motor M2 is stopped by operation of the phase difference motor control button S3, so that the opening angle θ of the opening portions 40c and 40d is maintained at the desired value. When the transmission of the drive force from the phase difference motor M2 to the second sun gear 66 is interrupted so that the second sun gear 66 is rotated only by the chopper motor M1, the first aperture controlling rotary plate 41 and the second aperture controlling rotary plate 42 are rotated in the same direction at the same speed while maintaining the desired opening angle θ. Since the rotation speed of the chopper motor M1 and the phase difference motor M2 can be controlled by the operation of the chopper motor control button S2 and the phase difference motor control button S3, respectively, an operator (user) can manually and freely control the quantity of light to be transmitted to the light guide 20.

In the first embodiment of the present invention, the main bodies of the chopper motor M1 and the phase difference motor M2 of the drive mechanism DM1 do not rotate, and hence, the harnesses M1a and M2a thereof are not twisted or bent in accordance with the rotation of the chopper motor M1 and the phase difference motor M2. Therefore, it is not necessary to provide a specific device to prevent an interference of the harnesses M1a and M2a.

Figure 6:
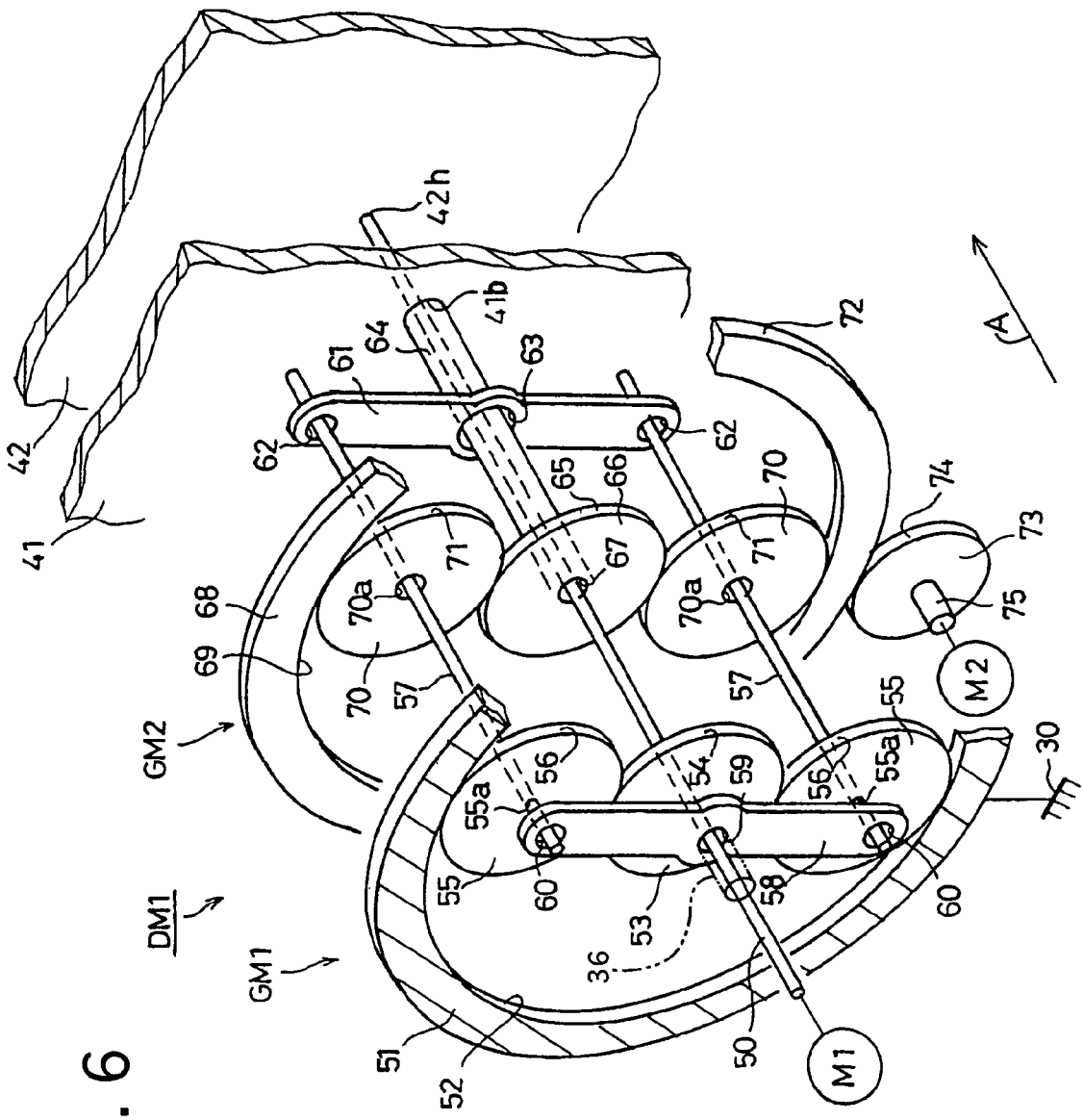
FIG. 6 is an exploded perspective view of a first modification of a first embodiment of the invention.
Figure 7:
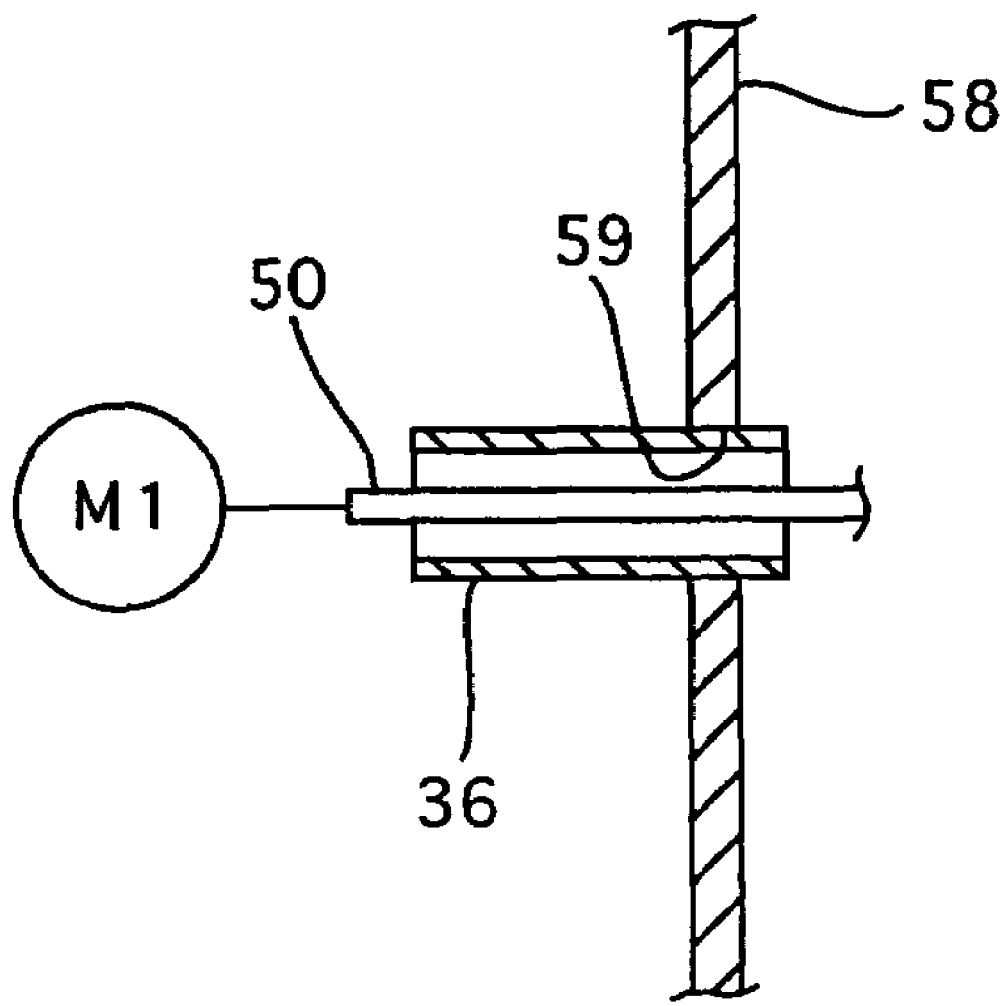
FIG. 7 is an enlarged sectional view of a first carrier and a stationary bearing in the first modification of the first embodiment of the present invention.
Figure 8:
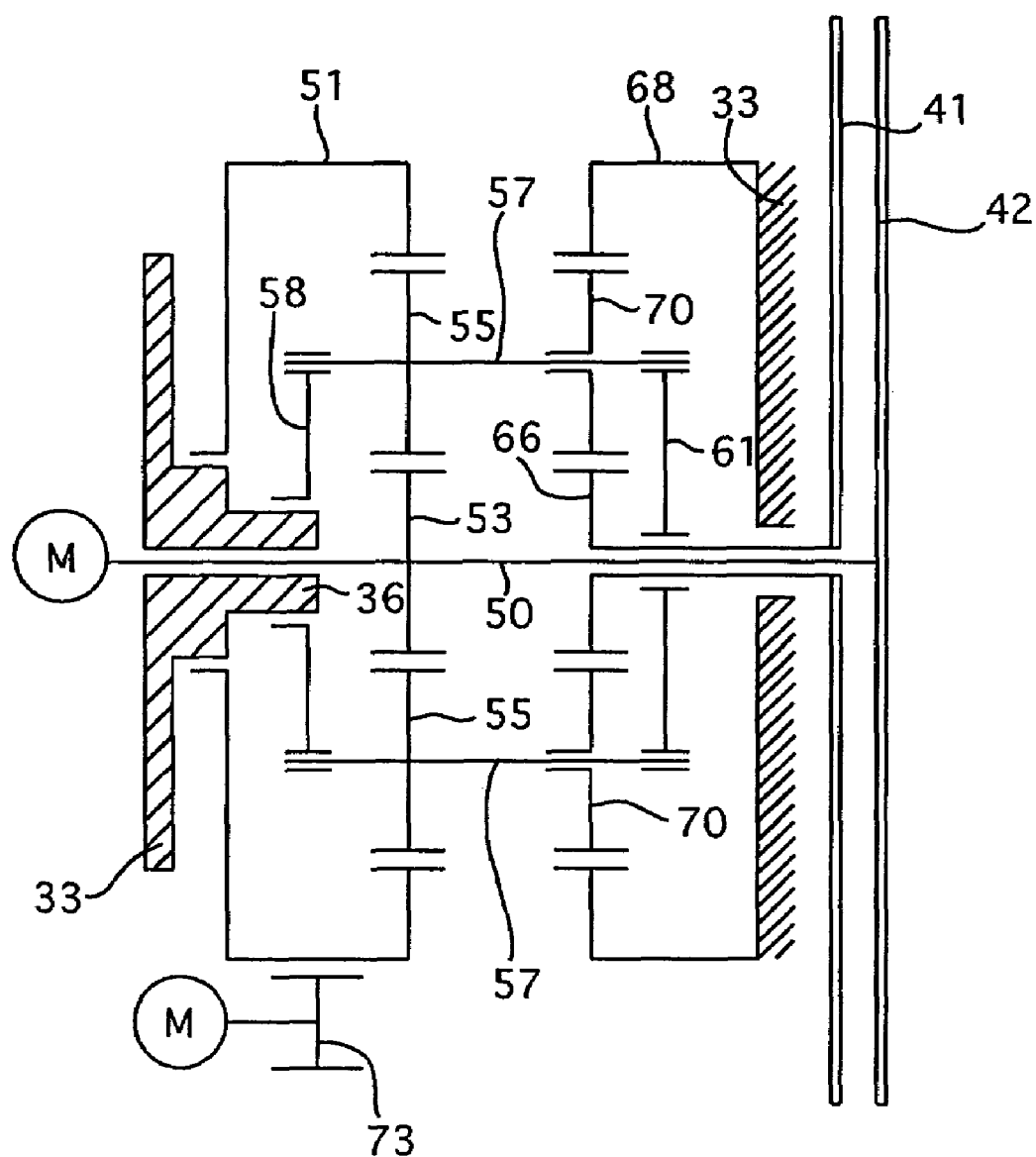
FIG. 8 is a schematic view of a drive mechanism and its surroundings in the first modification of the first embodiment of the present invention.

FIGS. 6 through 8 show a modified embodiment of the first embodiment.

In this modification, a cylindrical stationary bearing (carrier shaft) 36 having open ends and provided coaxial with the drive shaft 50 extends from the casing 33, as indicated by phantom lines in FIG. 6, and as shown in FIGS. 7 and 8. The stationary bearing 36 is located around the end of the drive shaft on the chopper motor M1 side. The stationary bearing 36 is relatively rotatably fitted in the center hole (rotation center hole) 59 of the first carrier 58. The outer diameter of the stationary bearing 36 is identical to the diameter of the center hole 59. The first carrier 58 is relatively rotatably supported by the stationary bearing 36.

Furthermore, the rotary cylinder (carrier bearing) 64 whose outer diameter is smaller than the diameter of the mounting hole 63 is relatively rotatably fitted in the center mount hole (rotation center hole) 63 of the second carrier 61.

Figure 4:
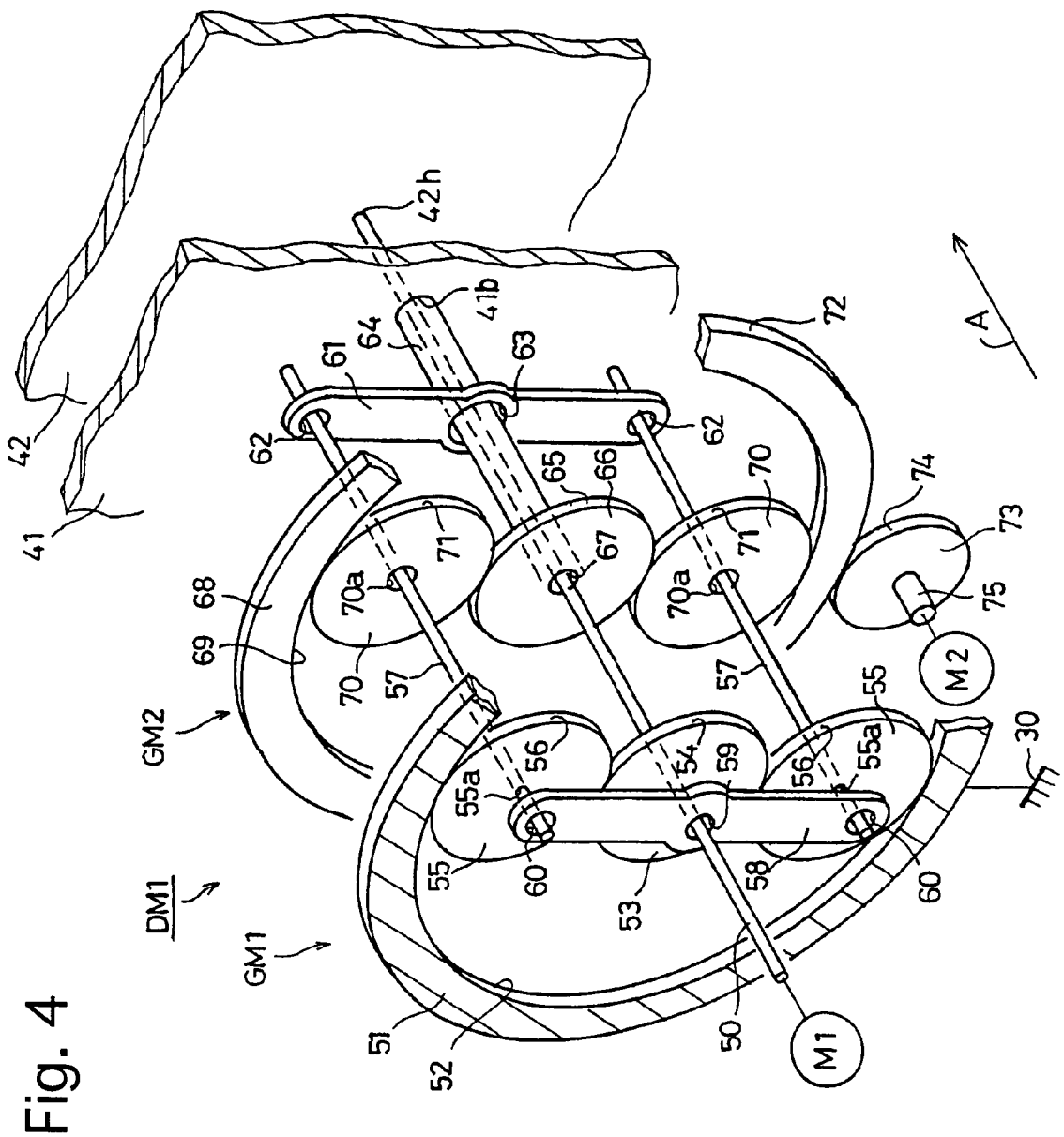
FIG. 4 schematically shows an exploded perspective view of a drive mechanism.
Figure 5:
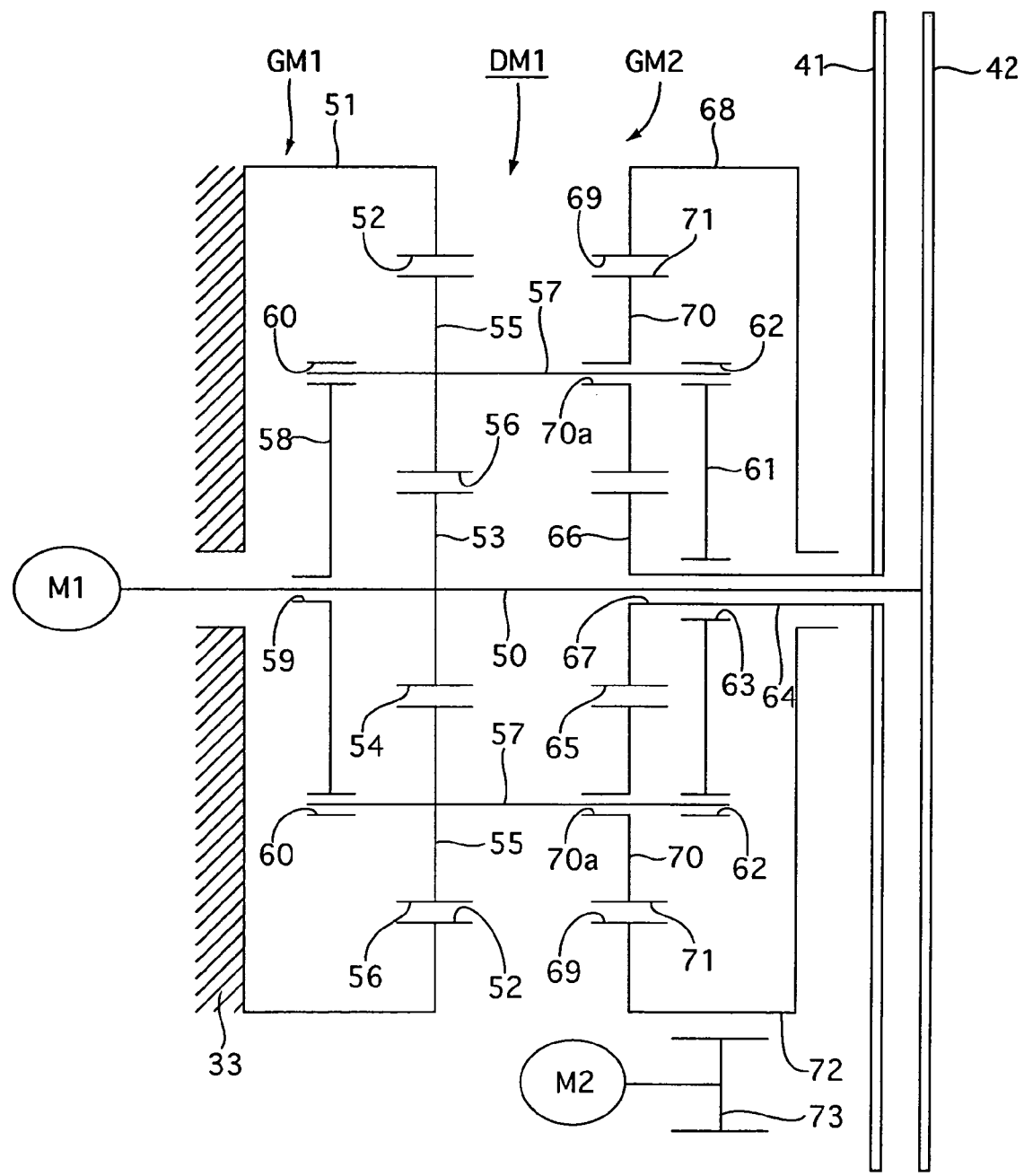
FIG. 5 is a schematic view of a drive mechanism and its surroundings.

The drive mechanism DM1 in the first alternative of the first embodiment operates in the same way as the drive mechanism DM1 shown in FIGS. 4 and 5. Since the first carrier 58 is supported by the stationary bearing 36, no undesirable oscillation of the first carrier 58 takes place during the operation of the drive mechanism DM1. Therefore, it is possible to more precisely operate the first aperture controlling rotary plate 41 and the second aperture controlling rotary plate 42 than the drive mechanism DM1 shown in FIGS. 4 and 5. Furthermore, no accidental flickering of the illumination light occurs. Moreover, since the first aperture controlling rotary plate 41 and the second aperture controlling rotary plate 42 can be precisely operated, it is possible to control the phase difference of the first aperture controlling rotary plate 41 and the second aperture controlling rotary plate 42 more accurately. As a result, it is possible to reduce the opening area (to increase the shutter speed).

Figure 9:
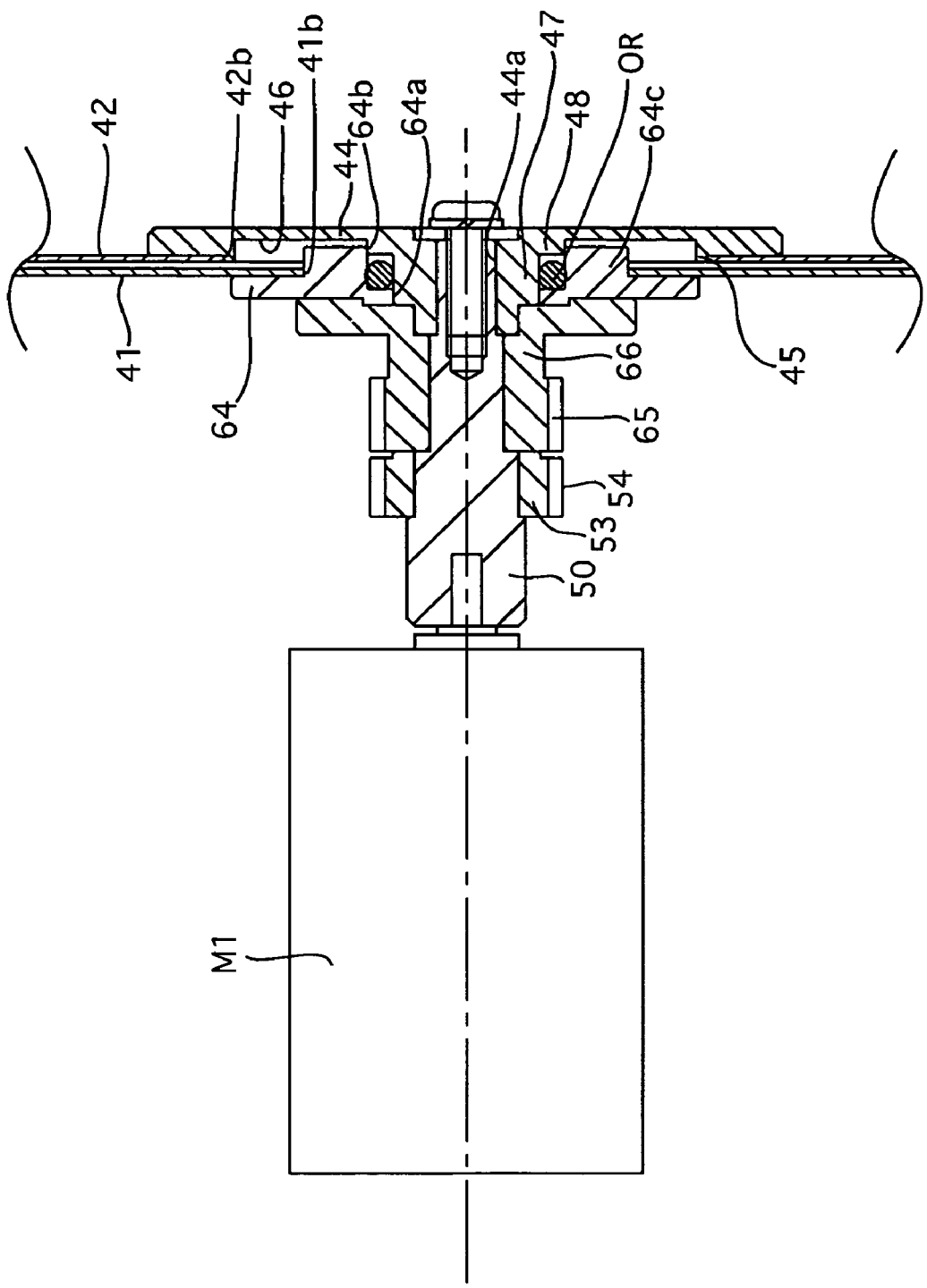
FIG. 9 is an enlarged longitudinal sectional side view of a drive mechanism in a second modification of the first embodiment, wherein the first internal tooth gear, the first carrier, the first planet gear, the second internal tooth gear, and the second planet gear removed for clarity.

FIG. 9 shows a second modification of the first embodiment.

In the second modification, the drive mechanism DM1 is improved so that the first aperture controlling rotary plate 41 and the second aperture controlling rotary plate 42 do not undesirably oscillate.

The end of the drive shaft 50 adjacent to the second aperture controlling rotary plate 42 is fitted and secured in the center hole 44a of the supporting disc member (second support member) 44. The supporting disc member 44 is provided, on the surface thereof on the chopper motor M2 side, with an annular projection 45 having an axis located on the axis of the drive shaft 50. The annular projection 45 is fitted and secured to a center hole 42b of the second aperture controlling rotary plate 42 which is circular in a front elevation. The supporting disc member 44 is provided, on the surface thereof on the chopper motor M2 side, with an annular recess 46 on the inner side of the annular projection 45. The supporting disc member 44 is provided with two stepped portions defined by annular cylindrical projections (rotation center projections) 47 and 48.

A rotary cylinder (first support member) 64 integral with the second sun gear 66 is provided with a center hole (support hole) 64a in which the stepped portion 47 of the supporting disc member 44 is relatively rotatably fitted. The rotary cylinder 64 is provided with an annular cylindrical recess (support hole) 64b having an axis located on the axis of the rotary cylinder 64. The rotary cylinder 64 is also provided with an annular projection 64c which is relatively rotatably fitted in the annular recess 46 of the supporting disc member 44.

An O-ring (annular support member) OR made of a frictional and viscous material (e.g., rubber material such as NBR, H.NBR, Si, fluorine, urethane, PTFE) is inserted in an annular space (annular clearance) defined between the annular recess 64b of the rotary cylinder 64 and the annular stepped portions 47 and 48 of the supporting disc member 44, so that the O-ring OR is continuously and elastically in contact with the outer peripheral surface of the stepped portion 47 and the inner peripheral surface of the annular recess 64b. Consequently, no movement of the first aperture controlling rotary plate 41 and the second aperture controlling rotary plate 42 in the radial direction of the rotary cylinder 64 occurs. Note that the O-ring OR can be replaced with another ring, such as an X-ring or the like.

In the drive mechanism in which no movement of the first aperture controlling rotary plate 41 and the second aperture controlling rotary plate 42 in the radial direction of the rotary cylinder 64 occurs, the first aperture controlling rotary plate 41 and the second aperture controlling rotary plate 42 can be operated more precisely than the drive mechanism DM1 shown in FIGS. 4 and 5, and accordingly, no accidental flickering of the illumination light occurs. Moreover, since the first aperture controlling rotary plate 41 and the second aperture controlling rotary plate 42 can be precisely operated, it is possible to control the phase difference of the first aperture controlling rotary plate 41 and the second aperture controlling rotary plate 42 more accurately. As a result, it is possible to reduce the opening area (to increase the shutter speed).

Figure 10:
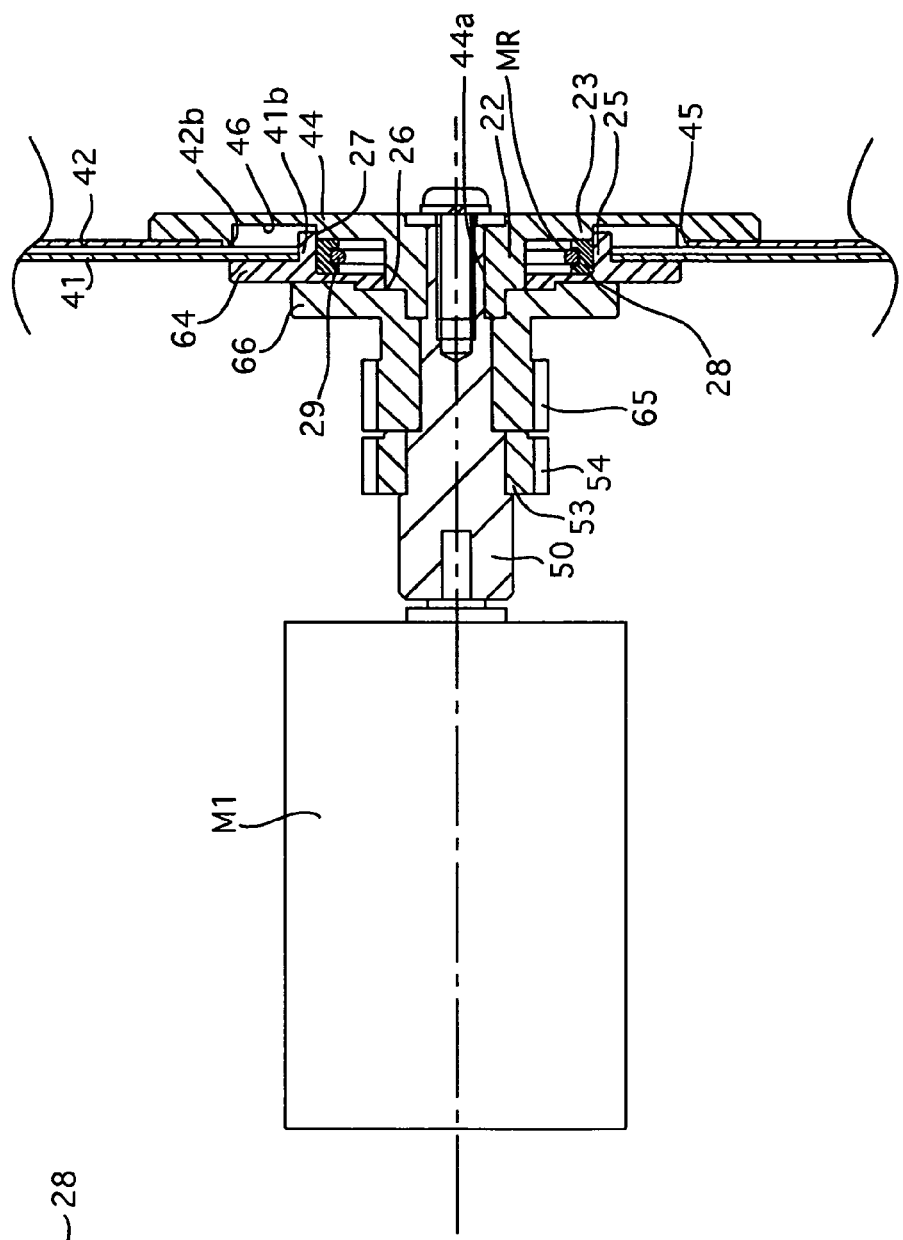
FIG. 10 is an enlarged longitudinal sectional side view of a drive mechanism in a third modification of the first embodiment, wherein the first internal tooth gear, the first carrier, the first planet gear, the second internal tooth gear, and the second planet gear are removed for clarity.
Figure 11:
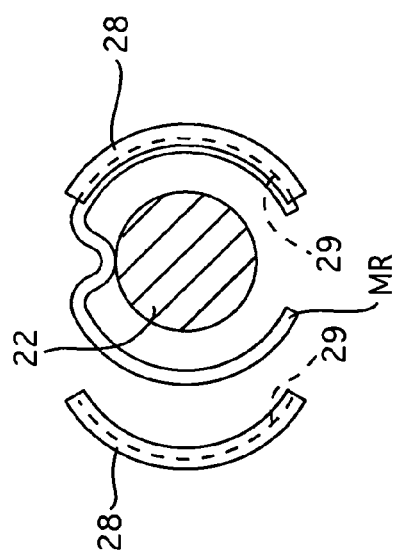
FIG. 11 is a partially broken, enlarged cross sectional front elevational view of arc-shaped abutment members, an M-ring, and annular stepped portions in a third modification of the first embodiment.

FIGS. 10 and 11 show a third modification of the first embodiment.

In the third modification, the drive mechanism DM1 is improved so that the first aperture controlling rotary plate 41 and the second aperture controlling rotary plate 42 do not undesirably oscillate. The elements corresponding to those in the second modification are designated with like reference numerals.

The supporting disc member (second support member) 44 is provided with two stepped portions defined by annular cylindrical projections (rotation center projections) 22 and 23. The rotary cylinder (first support member) 64 is provided with an annular projection 25 which is relatively rotatably fitted in the annular recess 46. In the center hole (support hole) 26 of the rotary cylinder 64 is relatively rotatably fitted the stepped portion 22 of the supporting disc member 44. The rotary cylinder 64 is provided with an annular cylindrical recess (support hole) 27 having an axis located on the axis of the rotary cylinder 64 (identical to the axis of the drive shaft 50).

The movement of the second sun gear 66 to which the rotary cylinder 64 is secured toward the chopper motor M1 side is restricted because the end face thereof on the chopper motor M1 side abuts against the first sun gear 53, but the movement of the second sun gear 66 in a direction opposite to the chopper motor M1 is not restricted.

However, a pair of arc-shaped abutment members (arc-shaped support members) 28 made of a frictional and viscous material are inserted in an annular space (annular clearance) defined between the annular recess 27 of the rotary cylinder 64 and the annular stepped portions 22 and 23 of the supporting disc member 44, so that the outer peripheral surfaces of the abutment members 28 are in contact with the annular recess 27. The number of the abutment members may be more than two. Furthermore, the right and left side surfaces of the arc-shaped abutment members 28 (with respect to FIG. 10) are brought into contact with the right side surface of the annular recess 27 of the rotary cylinder 64 and the left side surface of the annular stepped portion 23 of the supporting disc member 44, respectively. A substantially M-shaped M-ring (biasing device) MR made of an elastic material is provided around the annular stepped portion 22 and is elastically fitted in the arc-shaped grooves 29 provided in the inner peripheral surfaces of the arc-shaped abutment members 28. Due to the biasing force of the M-ring MR, the abutment members 28 are biased toward the outer periphery of the annular stepped portion 22. The outer peripheral surfaces of the arc-shaped abutment members 28 are elastically in contact with the inner peripheral surface of the annular recess 27, the right side surface of the annular recess 27 of the rotary cylinder 64, and the left aside surface of the stepped portion 23 of the supporting disc member 44. Consequently, no movement of the first aperture controlling rotary plate 41 and the second aperture controlling rotary plate 42 in the radial direction and axial direction of the rotary cylinder 64 occurs.

In the drive mechanism in which movement of the first aperture controlling rotary plate 41 and the second aperture controlling rotary plate 42 does not occur in the radial direction nor in the axial direction, of the rotary cylinder 64, the first aperture controlling rotary plate 41 and the second aperture controlling rotary plate 42 can be operated more precisely than the drive mechanism DM1 shown in FIG. 9, and accordingly, no accidental flickering of the illumination light occurs. Moreover, it is possible to control the phase difference of the first aperture controlling rotary plate 41 and the second aperture controlling rotary plate 42 more accurately, and it is possible to reduce the opening area of the rotary shutter 40 (to increase the shutter speed).

The second and third modifications can be applied to the first modification of the first embodiment.

A second embodiment of the present invention will be discussed with reference to FIGS. 12 to 14.

The second embodiment is different from the first embodiment only in the drive mechanism DM2. The elements corresponding to those in the first embodiment are designated with like reference numerals and no detailed explanation thereof will be given below.

A stationary bearing (gear bearing) AS secured to the casing 33 of the light source apparatus 30 is provided around the drive shaft 50 and the drive shaft of the chopper motor M1. The stationary bearing AS is in the form of a cylinder having open ends and is provided coaxial with the drive shaft 50 and the drive shaft of the chopper motor M1. An internal/external tooth gear (first internal tooth gear) 80 is substantially cylindrical and is provided, on its end wall on the chopper motor M1 side, with a central cylindrical fitting portion 80a coaxial with the drive shaft 50 and integral with the internal/external tooth gear 80. The stationary bearing AS is fitted in the cylindrical fitting portion 80a so as to relatively rotate about the drive shaft 50. Note that the inner diameter of the cylindrical fitting portion 80a is substantially the same as the outer diameter of the stationary bearing AS. The internal/external tooth gear 80 is identical in diameter to the internal tooth gear 51 and is provided, on its end surface adjacent to the first aperture controlling rotary plate 41, with a circular opening coaxial with the drive shaft 50. Internal teeth 81 identical to the internal teeth 52 are formed along the entire periphery of the circular opening of the internal/external tooth gear 80. External teeth 82 identical to the external teeth 72 are formed on the outer peripheral surface of the end of the internal/external tooth gear 80 adjacent to the first aperture controlling rotary plate 41. The phase difference motor M2 is secured to the casing 33 of the light source apparatus 30. The external teeth 74 of the drive gear 73 which is driven by the phase difference motor M2 are in mesh with the external teeth 82.

The internal tooth gear (second internal tooth gear) 83 has an inner diameter identical to the internal/external tooth gear 68 and is provided on its inner peripheral surface with internal teeth 84 identical to the internal teeth 69 and coaxial with the second sun gear 66. The internal tooth gear 83 is secured to the casing 33 of the light source apparatus 30 and is not rotatable. The internal tooth gear 83 is hatched in FIG. 12 to indicate that it is a stationary member.

In the second embodiment, the internal/external tooth gear 80, the first sun gear 53, and the first planet gears 55 constitute a first planetary gear mechanism GM1 and the second sun gear 66, the internal/external tooth gear 83 and the second planet gears 70 constitute a second planetary gear mechanism GM2.

The rotational movement of the first aperture controlling rotary plate 41 and the second aperture controlling rotary plate 42 will be explained below.

First, the following explanation will be applied when the automatic light control switch S1 is turned ON.

When the controller 35 drives the chopper motor M1 in accordance with the brightness signal supplied from the CCD 16, the rotation of the chopper motor M1 is transmitted to the second sun gear 66 through the same route as that in the first embodiment. Consequently, the first sun gear 53, the second sun gear 66, and the second aperture controlling rotary plate 42 are all rotated at the speed SP1. If the controller 35 drives the phase difference motor M2 in a direction opposite to the chopper motor M1, in accordance with the brightness signal supplied from the CCD 16, the internal/external tooth gear 80 is rotated in a direction opposite to the rotational direction of the first planet gears 55, so that the rotating speed of the first planet gears 55 is increased. As a result, the rotation speed SP2 of the first sun gear 53 and the drive shaft 50 becomes higher than the rotation speed SP1 of the second sun gear 66. Consequently, a difference in the rotation speed is produced between the first aperture controlling rotary plate 41 and the second aperture controlling rotary plate 42, so that the opening angle θ of the opening portions 40c and 40d is varied in the range of 0 to 90 degrees. Thus, the quantity of light to be transmitted through the rotary shutter 40 is automatically changed to provide a desired brightness of the viewed site.

If the controller 35 rotates the phase difference motor M2 in the same direction as the chopper motor M1, in accordance with the brightness signal supplied from the CCD 16, the rotation direction of the internal/external tooth gear 80 is the same as the rotational direction of the first planet gears 55, so that the rotating speed of the first planet gears 55 is lower than that obtained when the phase difference motor M2 is stopped. Consequently, the rotation speed SP 3 of the first sun gear 53 and the drive shaft 50 is lower than SP1. As a result, a difference in rotation speed is produced between the first aperture controlling rotary plate 41 and the second aperture controlling rotary plate 42, so that the opening angle θ of the opening portions 40c and 40d is varied in the range of 0 to 90 degrees. Thus, the quantity of light to be transmitted through the rotary shutter 40 is automatically changed to provide a desired brightness to the viewed site.

When the automatic light control switch S1 is turned OFF and the chopper motor control button S2 and the phase difference motor control button S3 are operated, the manual light control can be carried out in the second embodiment.

To this end, the chopper motor control button S2 and the phase difference motor control button S3 are first manually operated to rotate the chopper motor M1 and the phase difference motor M2. When the opening angle θ of the opening portions 40c and 40d becomes a desired value, the phase difference motor control button S3 is operated to stop the phase difference motor M2. After that, the first sun gear 53 is rotated only by the chopper motor M1. When the phase difference motor M2 is stopped, the internal/external tooth gear 80 is fixed, and the drive mechanism DM2 operates using the drive force of the chopper motor M1 only, the first sun gear 53 and the second sun gear 66 are rotated in the same direction at the same speed SP1 and the first aperture controlling rotary plate 41 and the second aperture controlling rotary plate 42 are rotated in the same direction while maintaining the desired opening angle θ. Thus, an operator (user) can freely and manually adjust the quantity of illumination light to be transmitted to the light guide 20.

In the second embodiment, as the stationary bearing AS bears the cylindrical fitting portion 80a of the internal/external tooth gear 80, the weight of the internal/external tooth gear 80 is not applied to the drive shaft 50. Therefore, the load applied to the drive shaft 50 or the chopper motor M1 can be reduced in comparison with the drive mechanism DM1 in the first embodiment in which the weight of the internal/external tooth gear 68 is applied to the drive shaft 50 through the second planet gears 70.

Figure 15:
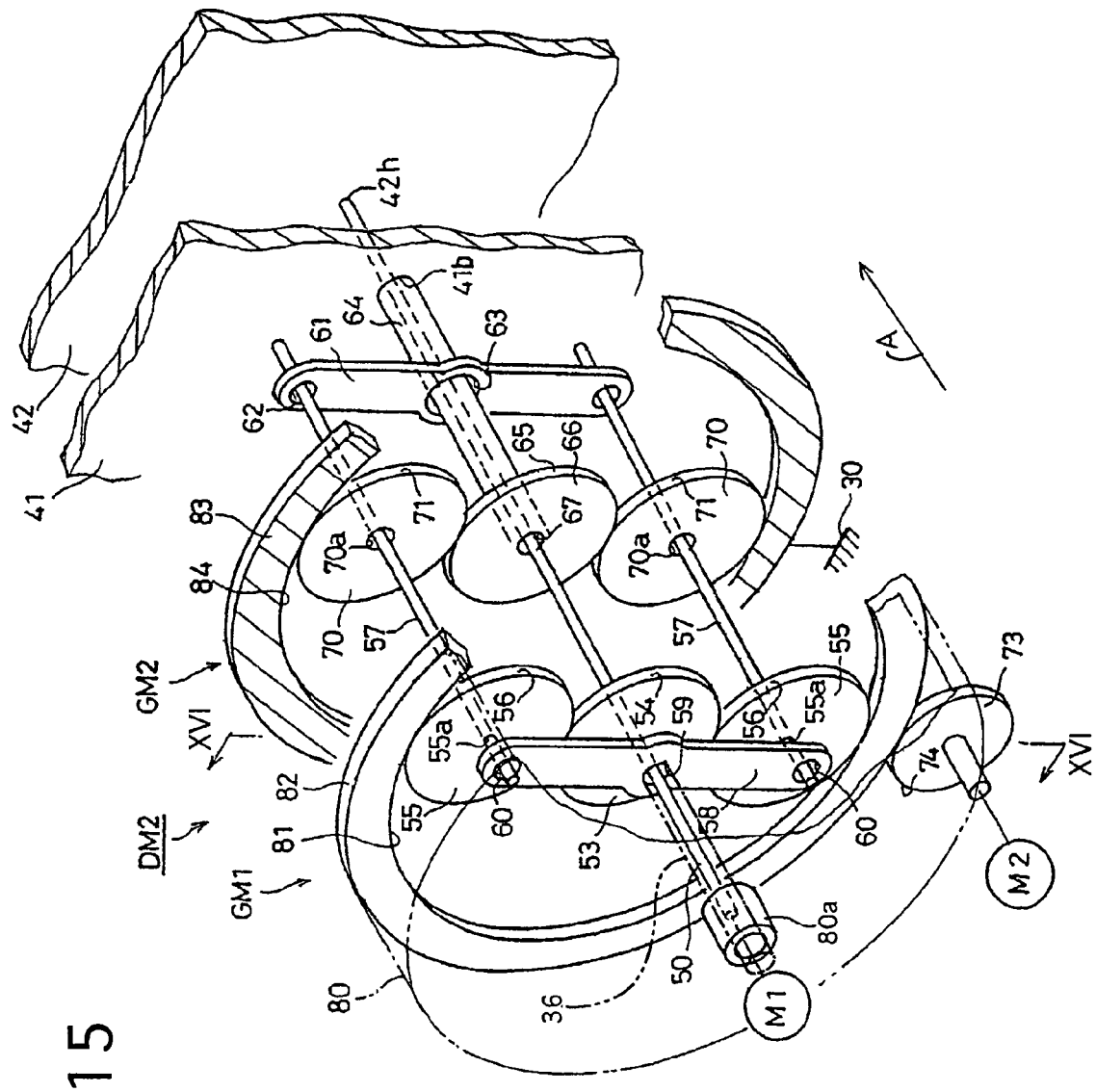
FIG. 15 is an exploded perspective view of a drive mechanism in a first modification of the second embodiment of the present invention.
Figure 16:
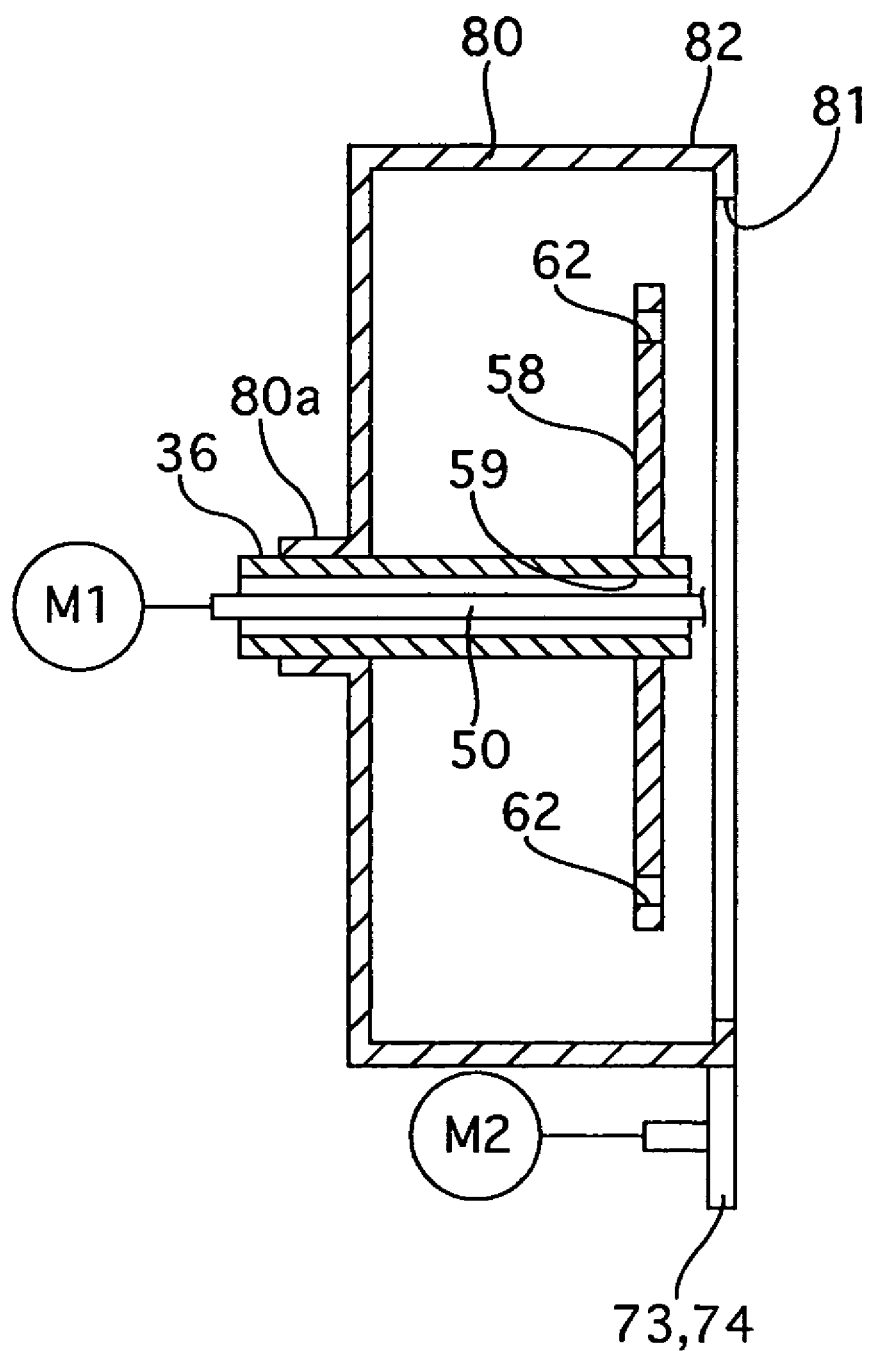
FIG. 16 is a sectional view taken along the line XVI-XVI in FIG. 15.

FIGS. 15 and 16 show a first modification of the second embodiment.

In this modification, a cylindrical stationary bearing (carrier bearing) 36 having open ends, and coaxial with the drive shaft 50, is provided around the end of the drive shaft 50 on the chopper motor M1 side, in place of the stationary bearing AS of the second embodiment. The stationary bearing 36 is formed integral with the casing 33 and is relatively rotatably fitted in the cylindrical fitting portion 80a and the center hole (rotation center hole) 59 of the first carrier 58. The outer diameter of the stationary bearing 36 is substantially the same as the inner diameter of the cylindrical fitting portion 80a and the diameter of the center hole 59. The cylindrical fitting portion 80a and the first carrier 58 are relatively rotatably supported by the stationary bearing 36.

Figure 12:
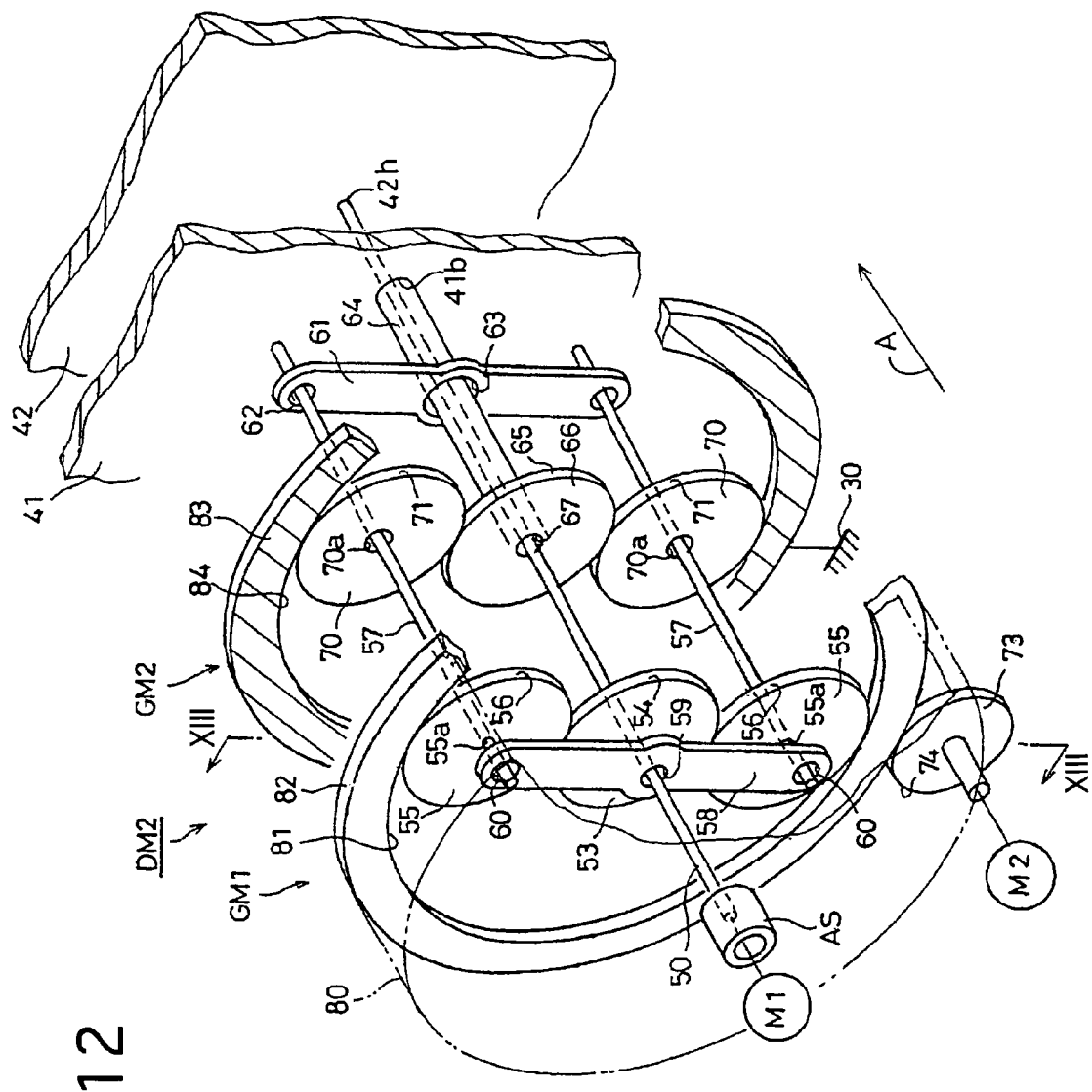
FIG. 12 is an exploded perspective view of a drive mechanism according to a second embodiment of the present invention.
Figure 13:
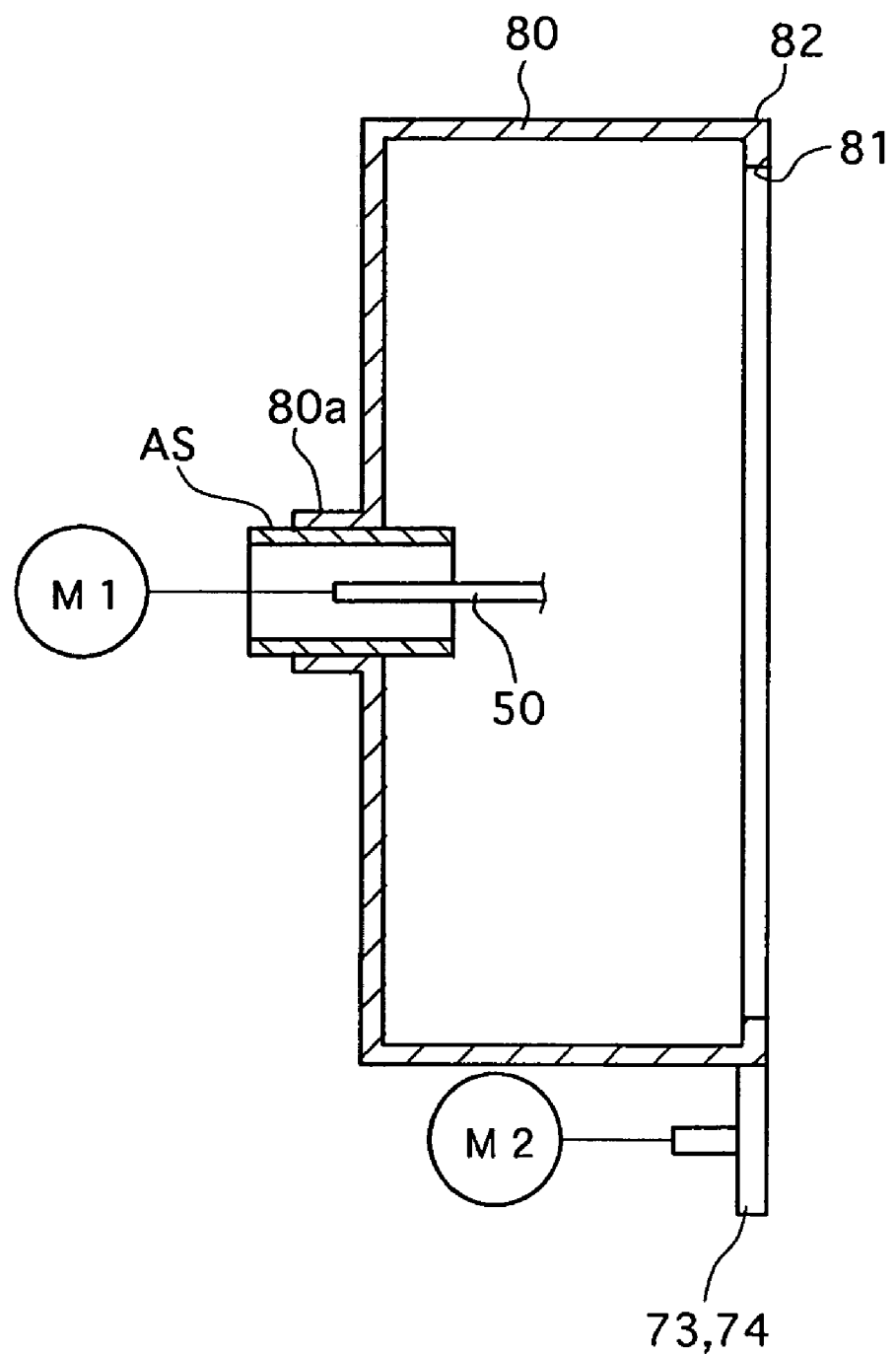
FIG. 13 is a sectional view taken along the line XIII-XIII in FIG. 12.
Figure 14:
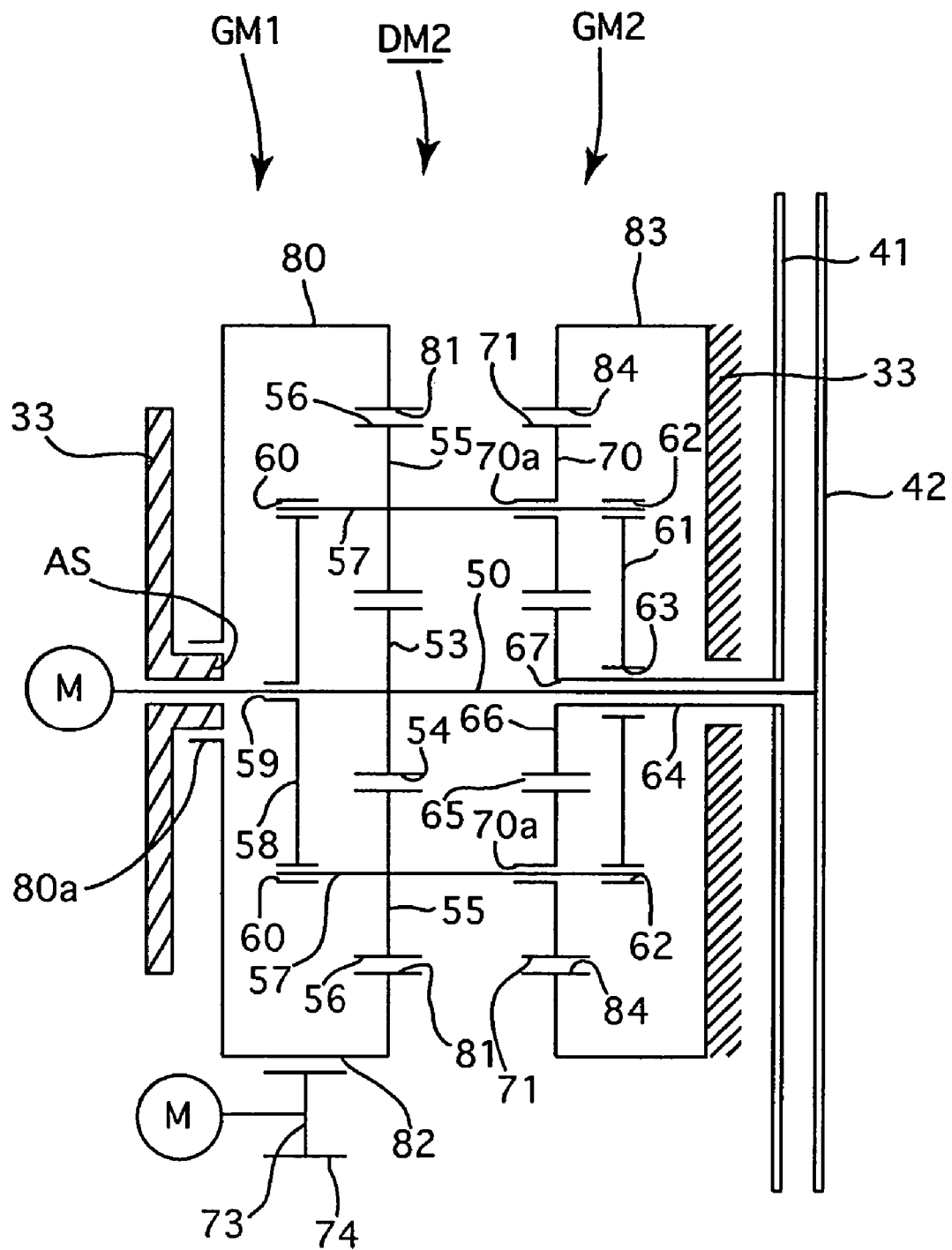
FIG. 14 is a schematic view of a drive mechanism and its surrounding members.

The drive mechanism DM2 in the first modification operates in the same way as the drive mechanism DM2 shown in FIGS. 12 to 14. It is possible to prevent the first carrier 58 from undesirably oscillating during the operation of the drive mechanism DM2 because the first carrier 58 is supported by the stationary bearing 36. Therefore, the first aperture controlling rotary plate 41 and the second aperture controlling rotary plate 42 can be operated more precisely than the drive mechanism DM2 shown in FIGS. 12 to 14, and accordingly no accidental flickering of the illumination light occurs. Moreover, it is possible to control the phase difference of the first aperture controlling rotary plate 41 and the second aperture controlling rotary plate 42 more accurately and to reduce the opening area (to increase the shutter speed).

Furthermore, as the stationary bearing 36 serves also as a bearing for the cylindrical fitting portion 80a of the internal/external tooth gear 80, the weight of the internal/external tooth gear 80 is not applied to the drive shaft 50, and accordingly, the load applied to the drive shaft 50 or the chopper motor M1 can be reduced. Since both the first carrier 58 and the cylindrical fitting portion 80a of the internal/external tooth gear 80 are supported by the stationary bearing 36, the number of components can be reduced.

Figure 17:
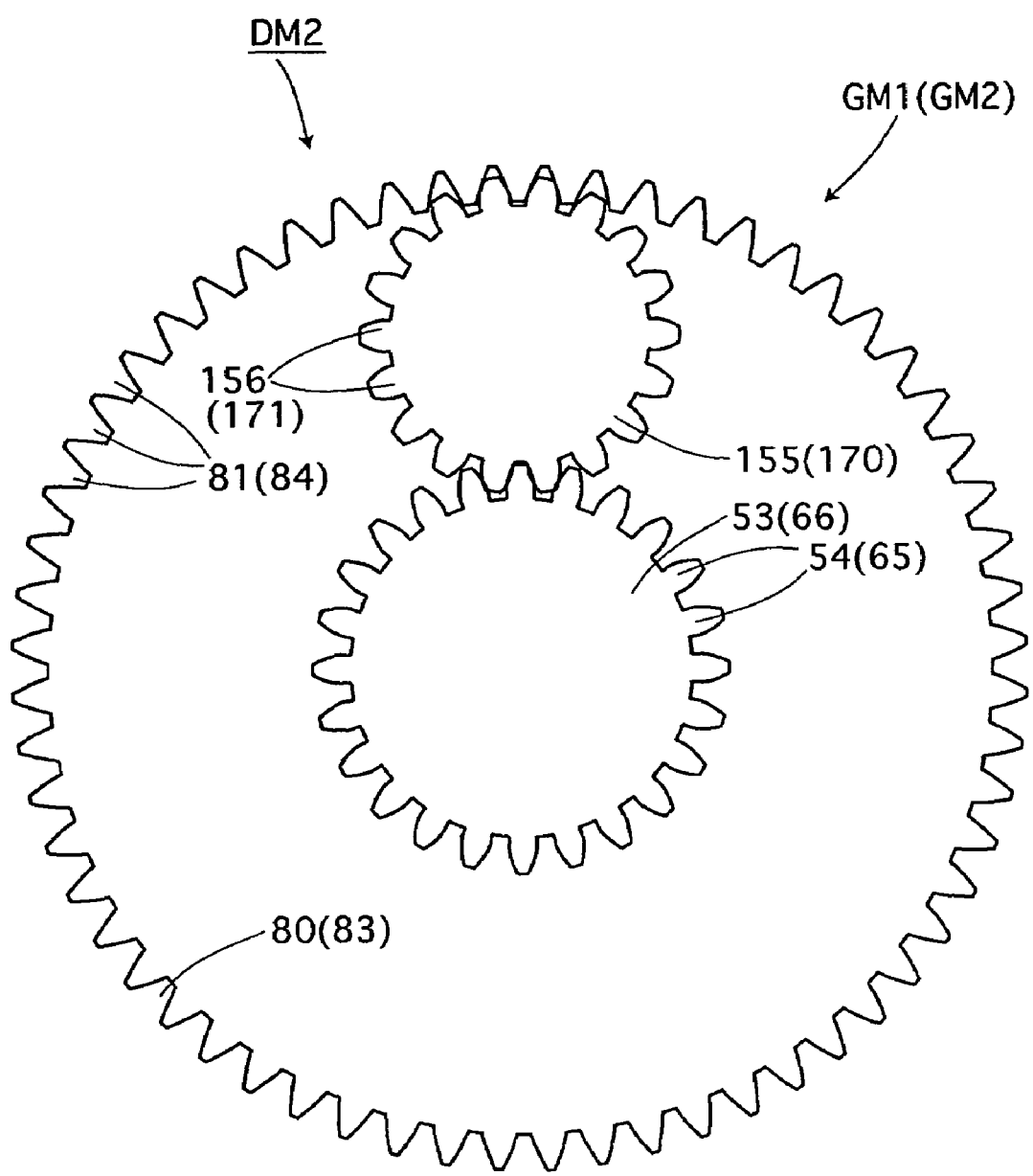
FIG. 17 is an enlarged front elevational view of main parts of a first planetary gear mechanism in a second modification of the second embodiment of the present invention.
Figure 18:
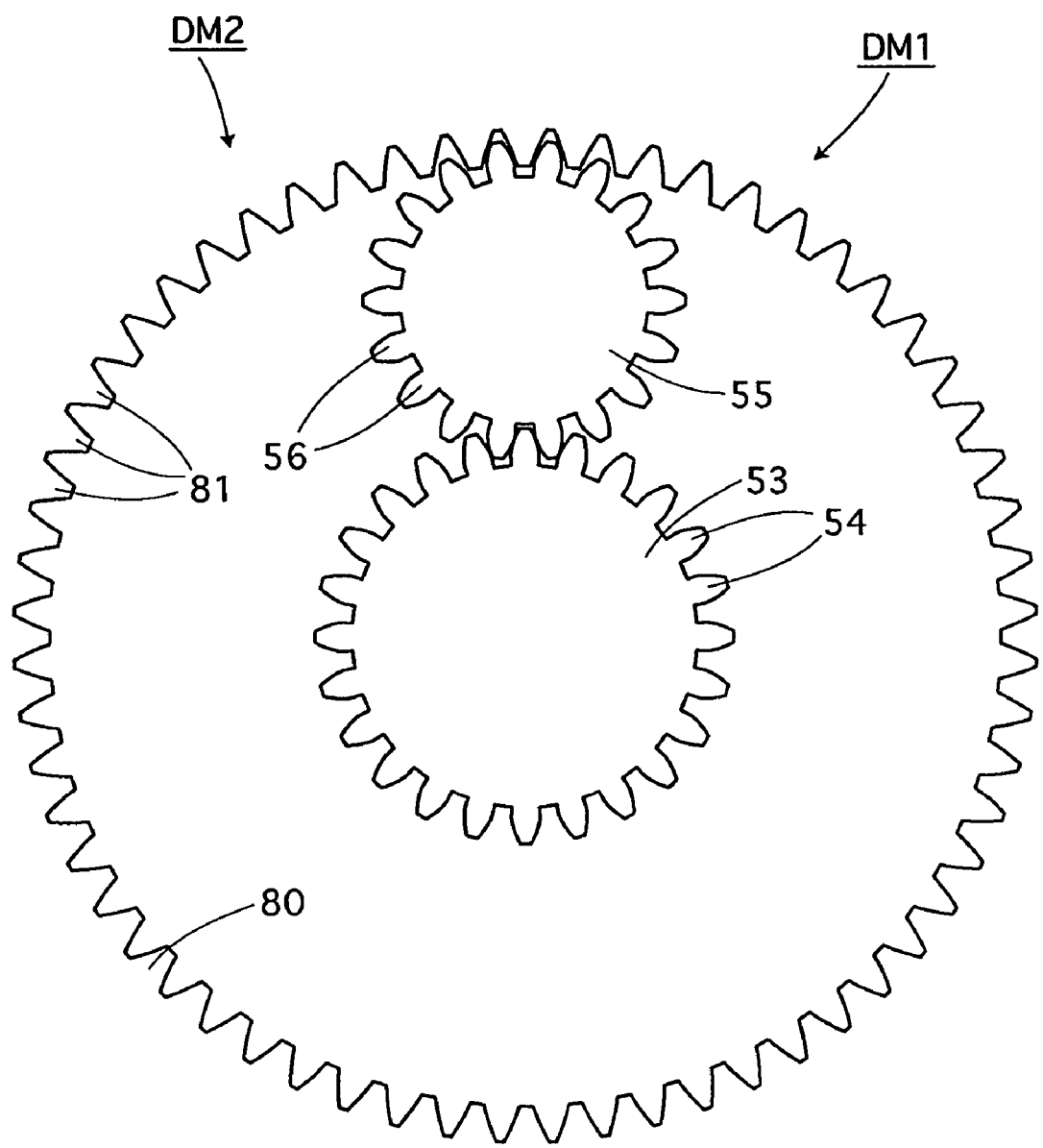
FIG. 18 is an enlarged front elevational view of a first planetary gear mechanism in first and second embodiments for comparison with the second modification of the first and second embodiments.

FIGS. 17 and 18 show a second modification of the second embodiment.

In this modification, the drive mechanism DM2 is improved by improving the first planet gears 55 and the second planet gears 70 so that the first aperture controlling rotary plate 41 and the second aperture controlling rotary plate 42 do not undesirably oscillate.

FIG. 18 shows the first sun gear 53, the first planet gears 55 (only one planet gear is shown) and the internal/external tooth gear 80. The internal teeth 81 of the internal/external tooth gear 80 and the external teeth 54 of the first sun gear 53 are respectively engaged with the adjacent external teeth 56 of the first planet gear 55. The first planet gear 55 is generally a standard gear made of a plastic or metallic material, and accordingly, backlash exists between the first planet gear 55 and the first sun gear 53 (gaps are formed in the radial direction of the first planet gear 55 between the adjacent teeth 56 of the first planet gear 55 and the external teeth 54 of the first sun gear 53). The second planet gear 70 is also generally a standard gear made of a plastic or metallic material. Backlash also exists between the second planet gear 70 and the second sun gear 66 (gaps are formed in the radial direction of the second planet gear 70 between the adjacent external teeth 71 of the second planet gear 70 and the external teeth 65 of the second sun gear 66).

As shown in FIG. 17, the number of the external teeth 156 of the first planet gear 155 in the first modification of the second embodiment is the same as that of the first planet gear 55 and the outer diameter of the first planet gear 155 is greater than that of the first planet gear 55. Likewise, the number of the external teeth 171 of the second planet gear 170 in the first modification of the second embodiment is the same as that of the second planet gear 70 and the outer diameter of the second planet gear 170 is greater than that of the second planet gear 70. The first planet gear 155 is identical to the second planet gear 170. Furthermore, the first planet gear 155 and the second planet gear 170 are made of a viscoelastic material, i.e., thermoplastic elastomer (TPE; e.g., styrene-based thermoplastic elastomer (TPS), olefin-based thermoplastic elastomer (TPO), polyurethane-based thermoplastic elastomer (TPU), polyester-based thermoplastic elastomer (TPEE), vinyl chloride-based thermoplastic elastomer (TPVC), polyamide-based thermoplastic elastomer (PEBAX)). Moreover, the first planet gear 155 and the second planet gear 170 are profile shifted gears which are shifted in the positive direction with respect to the first and second planet gears 55 and 70 that are standard gears having the same number of teeth and same module as those of the first and second planet gears 155 and 170. As can be understood from FIG. 17, no backlash exists between the first planet gear 155 and the first sun gear 53 (there is no gap in the radial direction of the first planet gear 155 between the adjacent external teeth 156 of the first planet gear 155 and the external teeth 54 of the first sun gear 53). Likewise, no backlash exists between the second planet gear 170 and the second sun gear 66 (there is no gap in the radial direction of the second planet gear 170 between the adjacent external teeth 171 of the second planet gear 170 and the external teeth 65 of the second sun gear 66).

In the first planet gear 155 and the second planet gear 170 constructed as described above, there is no backlash between the first planet gear 155 and the first sun gear 53 and between the second planet gear 170 and the second sun gear 66, and the first planet gear 155 and the second planet gear 170 are made of thermoplastic elastomer which exhibits a good viscoelasticity. Therefore, no oscillation of the first planetary gear mechanism GM1 and the second planetary gear mechanism GM2 during the operation of the drive mechanism DM2 occurs. Therefore, the first aperture controlling rotary plate 41 and the second aperture controlling rotary plate 42 can be operated more precisely than the drive mechanism DM2 shown in FIGS. 12 to 14, and accordingly, no accidental flickering of the illumination light occurs. Moreover, it is possible to control the phase difference of the first aperture controlling rotary plate 41 and the second aperture controlling rotary plate 42 more accurately, and it is possible to reduce the opening area (to increase the shutter speed) of the rotary shutter 40.

The first planet gear 155 and the second planet gear 170 can be applied to the first modification of the second embodiment and the first embodiment including the modified embodiments thereof.

Furthermore, the second and third modifications of the first embodiment can be applied to the second embodiment including the modified embodiments thereof.

Figure 19:
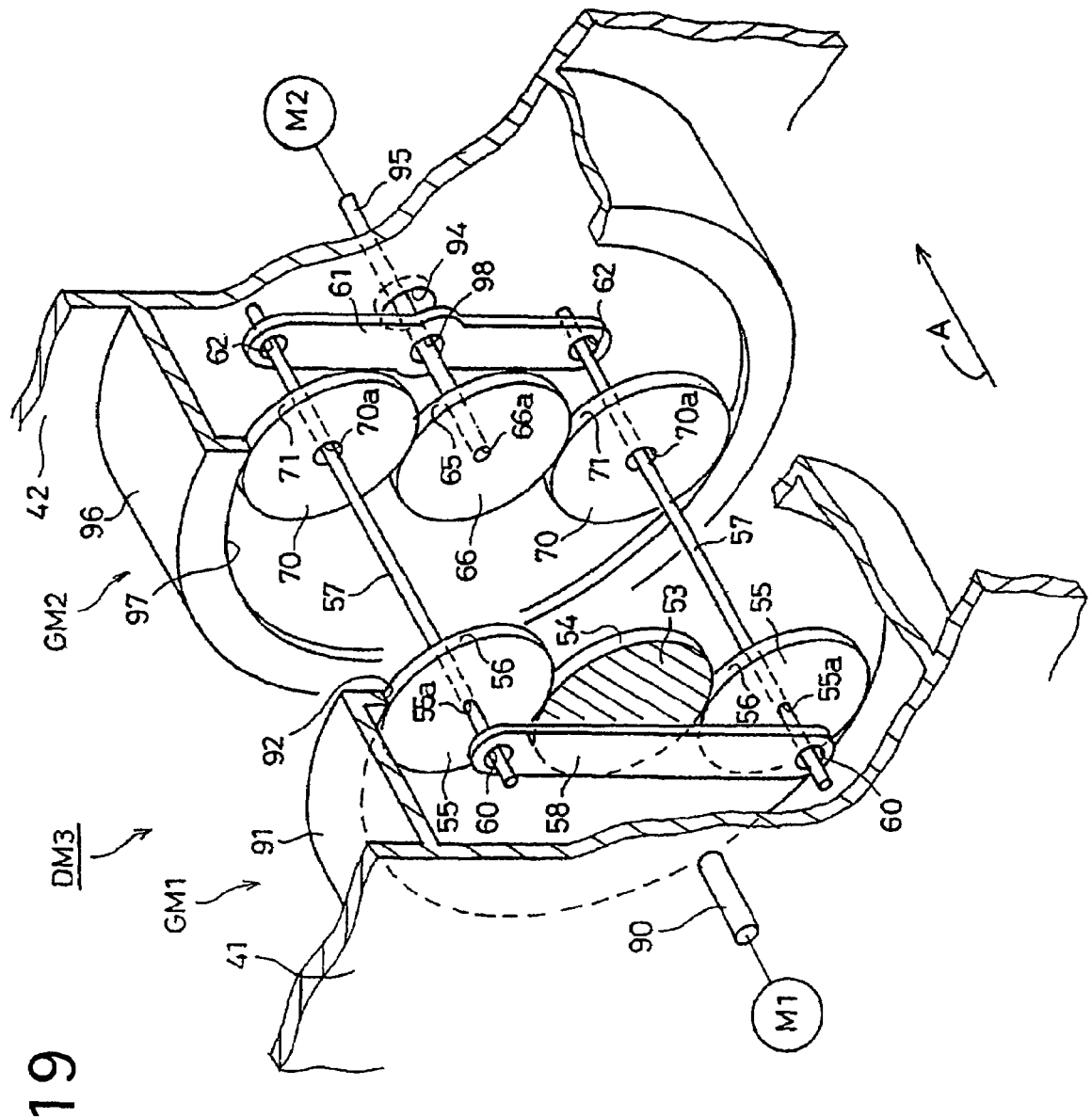
FIG. 19 is an exploded perspective view of a drive mechanism in a third embodiment of the present invention.
Figure 20:
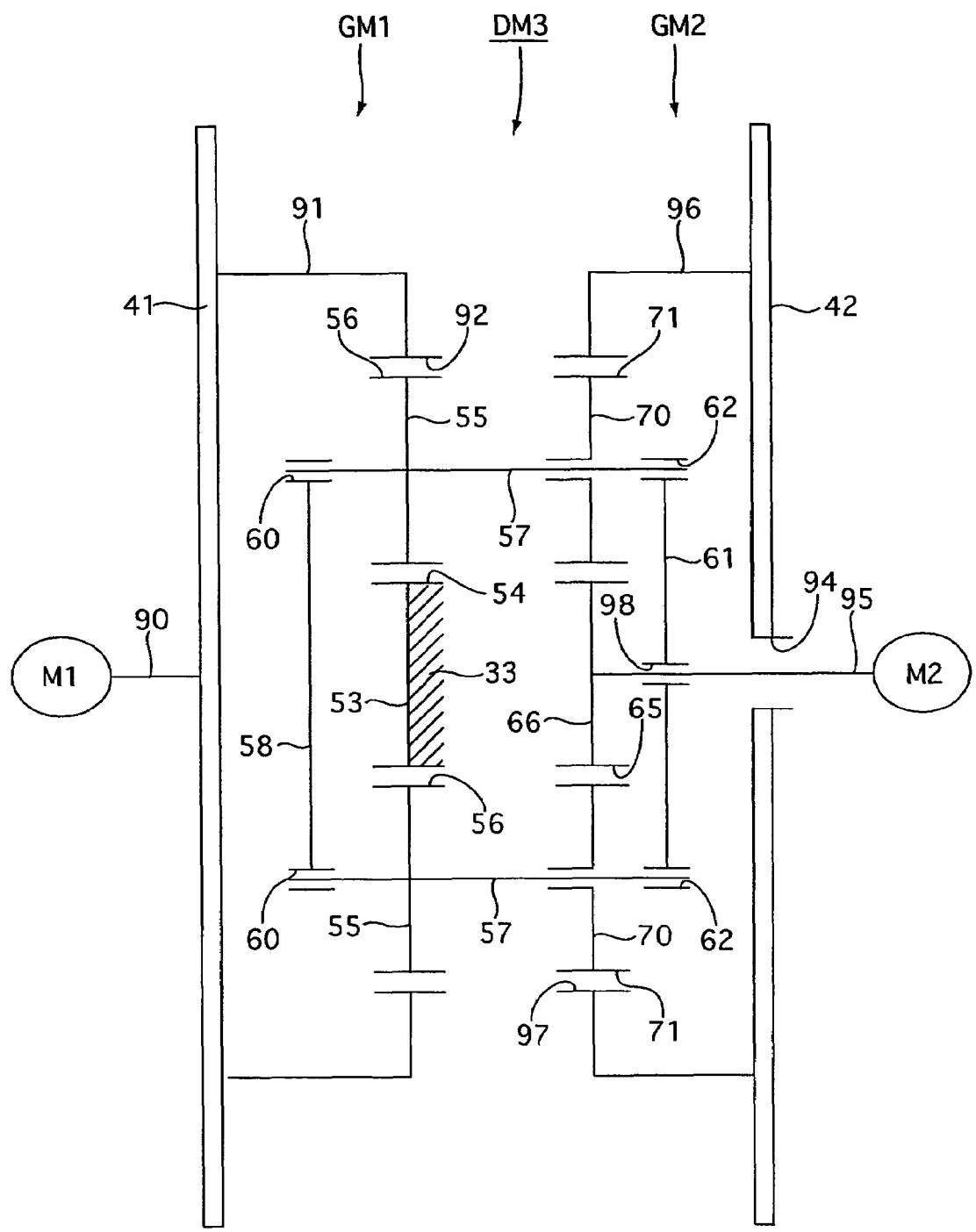
FIG. 20 is a schematic view of a drive mechanism and its surrounding members.

A third embodiment of the present invention will be discussed below with reference to FIGS. 19 and 20. The elements corresponding to those in the first embodiment are designated with like reference numerals, and no detailed explanation thereof will be given.

The drive mechanism DM3 in the third embodiment is constructed as follows.

A drive shaft (rotation shaft) 90 which extends perpendicular to the first aperture controlling rotary plate 41 (parallel with the light axis 31a), and is provided on the center of the first aperture controlling rotary plate 41, is rotated about its axis by the chopper motor M1 secured to the casing 33 of the light source apparatus 30. The first aperture controlling rotary plate 41 is provided, on its surface opposed to the second aperture controlling rotary plate 42 (opposite to the drive shaft 90), with a first internal/external tooth gear (first internal tooth gear) 91, which is substantially in the form of a cylinder coaxial with the drive shaft 90. The end surface of the first internal tooth gear 91 on the second aperture controlling rotary plate 42 side is provided with a circular opening coaxial with the drive shaft 90. An internal tooth gear 92 identical to the internal tooth gear 52 is formed along the circular opening. The first sun gear 53 secured to the casing 33 of the light source apparatus 30 is arranged coaxially to the internal tooth gear 92 in the circular opening of the first internal tooth gear 91. The first sun gear 53 is hatched in FIG. 19 to indicate that the first sun gear 53 is a stationary member. The first sun gear 53 in the third embodiment has no center hole unlike the first sun gear 53 in the first embodiment. The external teeth 54 of the first sun gear 53 and the internal teeth 92 of the first internal/external tooth gear 91 are in mesh with the external teeth 56 of the two first planet gears 55. The two first planet gears 55 are arranged symmetrically with respect to the first sun gear 53. The driven shafts 57 extending through (secured to) the first planet gears 55 are interconnected at the ends thereof adjacent to the chopper motor M1 by the first carrier 58.

The second aperture controlling rotary plate 42 is provided on its center with a circular through-hole 94 through which the drive shaft (rotation shaft) 95 coaxial with the drive shaft 90 (parallel with the optical axis 31a) extends. The drive shaft 95 is connected, at the end thereof opposite to the chopper motor M1, to the phase difference motor M2 secured to the housing 33 of the light source apparatus 30, so that the drive shaft 95 is driven by the phase difference motor M2. The other end of the drive shaft 95 opposite to the phase difference motor M2 is fitted and secured to the center mount hole 66a formed in the second sun gear 66. The second aperture controlling rotary plate 42 is provided, on its end surface adjacent to the first aperture controlling rotary plate 41, with a substantially cylindrical second internal/external tooth gear (second internal tooth gear) 96 coaxial with the first internal/external tooth gear 91. The second internal/external tooth gear 96 is provided on its end face adjacent to the first aperture controlling rotary plate 41 with a circular opening which is coaxial with the drive shaft 95.

The internal teeth 97 identical to the internal teeth 92 are formed along the circular opening of the second internal/external tooth gear 96. The external teeth 65 of the second sun gear 66 and the internal teeth 97 of the second internal/external tooth gear 96 are in mesh with the external teeth 71 of the two second planet gears 70. The two second planet gears 70 are arranged symmetrically with respect to the second sun gear 66. The driven shafts 57 relatively rotatably extend through the center holes 70a of the two second planet gears 70. The ends of the driven shafts 57 on the phase difference motor M2 side are interconnected by the second carrier 61. The second carrier 61 is provided on its center (rotation center) with a circular through-hole (rotation center hole) 98 in which the drive shaft 95 relatively rotatably extends.

In the third embodiment, the first internal/external tooth gear 91, the first sun gear 53, and the first planet gears 55 constitute the first planetary gear mechanism GM1 and the second sun gear 66, the second internal/external tooth gear 96 and the second planet gear 70 constitute the second planetary gear mechanism GM2.

The operation of the drive mechanism DM3 and the rotational movement of the first aperture controlling rotary plate 41 and the second aperture controlling rotary plate 42 will be explained below.

First, the following explanation will be applied when the automatic light control switch S1 is turned ON.

When the controller 35 drives the chopper motor M1 in accordance with the brightness signal supplied from the CCD 16, the first internal/external tooth gear 91 is rotated at the speed SP1 and the first planet gears 55 revolve in the same direction as the first internal/external tooth gear 91 while rotating in a direction opposite to the direction of the first internal/external tooth gear 91. Consequently, the second planet gears 70 rotate and revolve at the same speed and in the same direction as the first planet gears 55, and the second internal/external tooth gear 96 is rotated in the same direction as the first internal/external tooth gear 91 at the speed SP1.

If the controller 35 rotates the phase difference motor M2 in the same direction as the chopper motor M1, in accordance with the brightness signal supplied from the CCD 16, the rotation speed of the second planet gears 70 is increased because the rotation speed of the second sun gear 66 is increased. As a result, the second internal/external tooth gear 96 is rotated in the same direction as the first internal/external tooth gear 91 at a speed SP2 higher than SP1. Consequently, a difference in rotation speed is produced between the first aperture controlling rotary plate 41 and the second aperture controlling rotary plate 42, so that the opening angle θ of the opening portions 40c and 40d is varied in the range of 0 to 90 degrees. Thus, the quantity of light to be transmitted through the rotary shutter 40 is automatically changed to provide a desired brightness to the viewed site.

If the controller 35 drives the phase difference motor M2 in a direction opposite to the chopper motor M1, in accordance with the brightness signal supplied from the CCD 16 to thereby rotate the second sun gear 66 in the same direction as the rotation direction of the second planet gears 70, the rotation speed of the second planet gears 70 is decreased. As a result, the second internal/external tooth gear 96 is rotated at a speed SP3 lower than SP1 in the same direction as the first internal/external tooth gear 91. Consequently, a difference in the rotation speed is produced between the first aperture controlling rotary plate 41 and the second aperture controlling rotary plate 42, so that the opening angle θ of the opening portions 40c and 40d is varied in the range of 0 to 90 degrees. Thus, the quantity of light to be transmitted through the rotary shutter 40 is automatically changed to provide a desired brightness to the viewed site.

In the third embodiment, when the automatic light control switch is turned OFF and the chopper motor control button S2 and the phase difference motor control button S3 are operated, the manual light control can be carried out.

To this end, the chopper motor control button S2 and the phase difference motor control button S3 are first manually operated to rotate the chopper motor M1 and the phase difference motor M2. When the opening angle θ of the opening portions 40c and 40d becomes a desired value, the phase difference motor control button S3 is operated to stop the phase difference motor M2. Thereafter, the first internal/external tooth gear 91 and the second internal/external tooth gear 96 are rotated only by the chopper motor M1. When the phase difference motor M2 is stopped, the first internal/external tooth gear 91 and the second internal/external tooth gear 96 are rotated in the same direction at the same speed by the chopper motor M1. Consequently, the first aperture controlling rotary plate 41 and the second aperture controlling rotary plate 42 are rotated while maintaining the desired opening angle θ. Thus, an operator can freely and manually adjust the quantity of illumination light to be transmitted to the light guide 20.

The same effect as that of the first embodiment can be obtained in the third embodiment of the invention.

Figure 21:
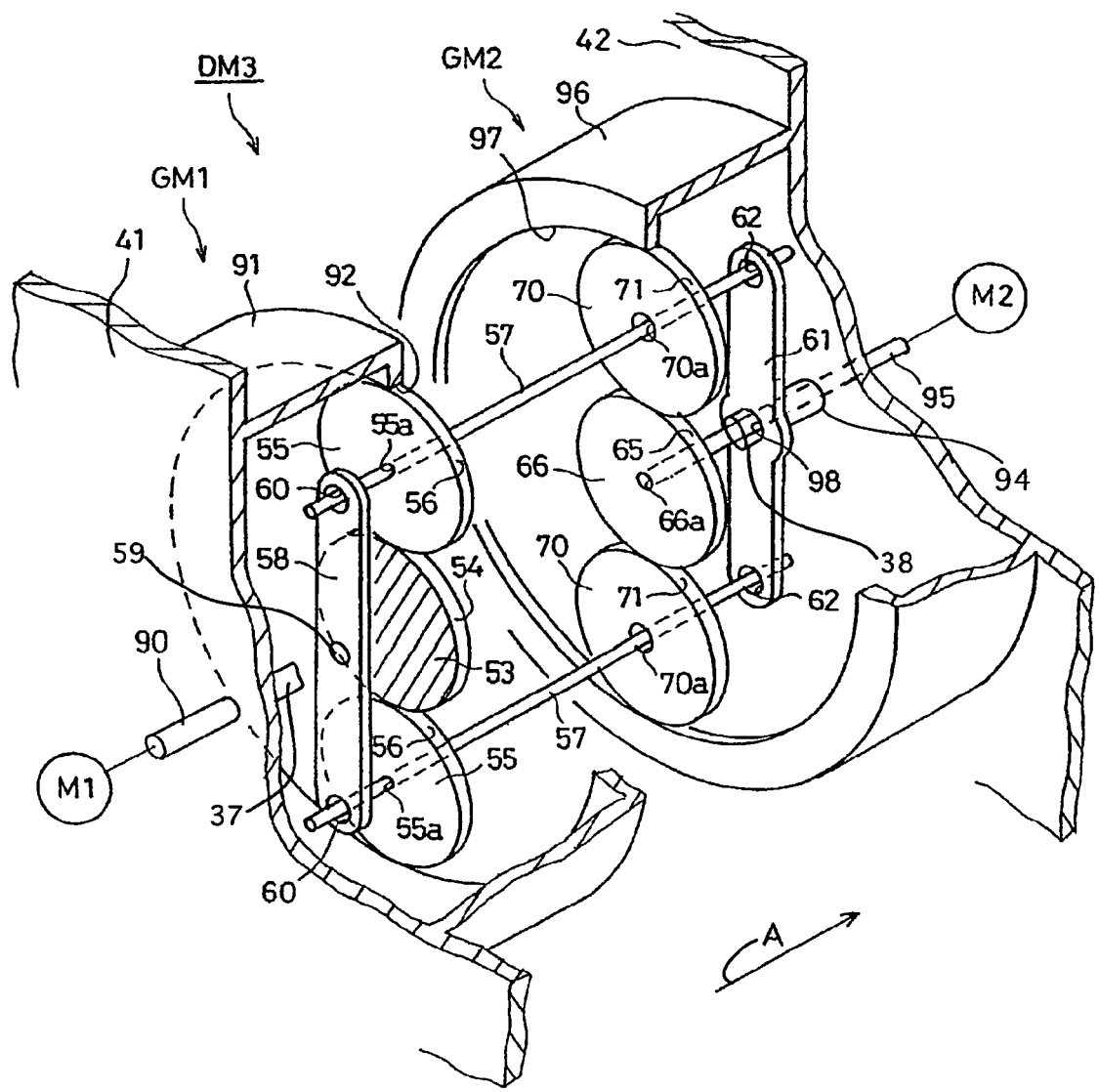
FIG. 21 is an exploded perspective view of a first modification of the third embodiment of the present invention.
Figure 22:
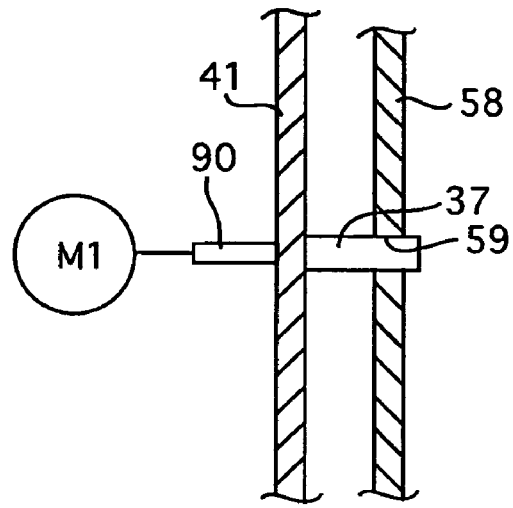
FIG. 22 is an enlarged sectional view of a first carrier and a rotatable bearing.
Figure 23:
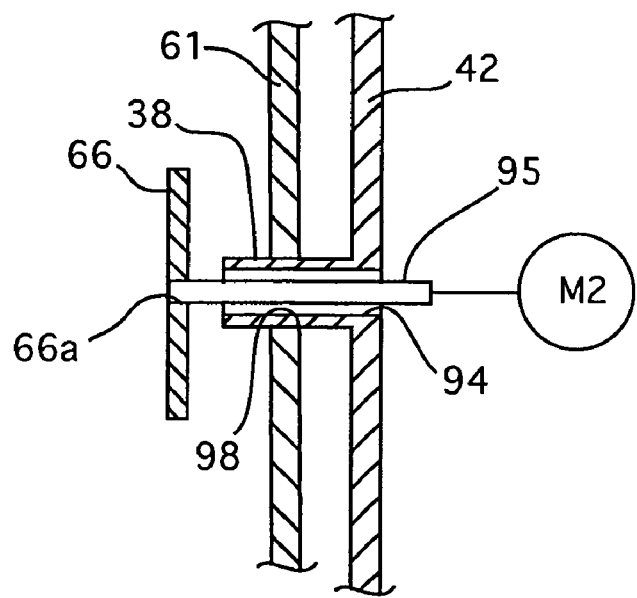
FIG. 23 is an enlarged sectional view of a second carrier and a rotatable bearing.

FIGS. 21 to 23 show a first modification of the third embodiment of the invention.

As shown in FIGS. 21 and 22, a cylindrical rotatable bearing (carrier bearing) 37, having a diameter identical to the diameter of a circular hole 59, is formed at the center (rotation center) of the first carrier 58, extends parallel with the driven shafts 57, is coaxial with the drive shaft 90, and is provided on the center portion of the surface of the first aperture controlling rotary plate 41 on the first carrier 58 side. The rotatable bearing 37 is relatively rotatably fitted in the center hole 59, and the first carrier 58 is relatively rotatably supported by the rotatable bearing 37. Furthermore, a cylindrical rotatable bearing (carrier bearing) 38, having an outer diameter substantially the same as the diameter of the through-hole 98, extends parallel with the driven shafts 57, is coaxial with the drive shaft 95, and is provided on the center portion of the surface of the second aperture controlling rotary plate 42 on the second carrier 61 side. As can be seen in FIGS. 21 and 23, the inside of the rotatable bearing 38 communicates with the through-hole 94 so that the drive shaft 95 extends through the inside of the rotatable bearing 38. The rotatable bearing 38 is relatively rotatably fitted in the through-hole 98 and the second carrier 61 is relatively rotatably supported by the rotatable bearing 38.

In the third embodiment of the present invention, since the first carrier 58 is supported by the rotatable bearing 37 and the second carrier 61 is supported by the rotatable bearing 38, no accidental oscillation of the first carrier 58 and the second carrier 61 takes place during the operation of the drive mechanism DM3.

Furthermore, the first planet gears 55 and the second planet gears 70 can be replaced with first planet gears 155 and the second planet gears 170. Moreover, the second and third modifications of the first embodiment can be applied to the third embodiment.

The present invention is not limited to the above-mentioned embodiments or modifications and can be modified without departing from the spirit of the present invention.

For example, in the first embodiment, the internal/external tooth gear 68 may be substantially in the form of a cylinder similar to the internal/external tooth gear 80 in the second embodiment, so that the cylindrical fitting portion thereof can be rotatably supported by the rotary cylinder 64. In this alternative, the weight of the internal/external tooth gear 68 is not applied to the drive shaft 50 through the second planet gears 70, and hence, the load applied to the drive shaft 50 or the chopper motor M1 can be reduced. Furthermore, in the third embodiment, it is possible to integrally provide the cylindrical fitting portions to the first aperture controlling rotary plate 41 and the second aperture controlling rotary plate 42 as in the second embodiment, so that the cylindrical fitting portions can be rotatably supported by the rotatable bearings 37 and 38, respectively. In this alternative, the weight of the first internal/external tooth gear 91 and the second internal/external tooth gear 96 is not applied to the drive shaft 90 and the drive shaft 95, through the first planet gears 55 and the second planet gears 70, respectively and accordingly, the load applied to the drive shaft 90, the drive shaft 95, the chopper motor M1 and the phase difference motor M2 can be reduced.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A light source apparatus for an electronic endoscope comprising:

a light source;

a rotary shutter having a rotation axis extending parallel with an optical axis of said light source, for one of intercepting and emitting illumination light emitted from said light source toward a light guide, said rotary shutter being provided with a pair of aperture controlling rotary plates, coaxial with each other, which are selectively capable of rotating one of relative to and together with each other, and which are each provided with light interception portions and opening portions alternately arranged in the rotation direction, wherein a combined opening angle of the opening portions of the rotary shutter is varied by a relative rotation of said pair of aperture controlling rotary plates, and wherein an amount of said light emitted is controlled by integral rotation of said pair of aperture controlling rotary plates;

a first planetary gear mechanism including a first internal tooth gear which is provided coaxial with the rotation axis of said rotary shutter, a first sun gear coaxial with an axis of said first internal tooth gear, and a first planet gear which simultaneously engages with the first internal tooth gear and the first sun gear;

a second planetary gear mechanism including a second internal tooth gear identical to said first internal tooth gear and coaxial with said rotation axis of said rotary shutter, a second sun gear identical to said first sun gear and coaxial with an axis of said second internal tooth gear, and a second planet gear identical to said first planet gear and which simultaneously engages with said second internal tooth gear and said second sun gear; and a carrier mechanism which holds said first and second planet gears in a same phase position, with respect to said first and second internal tooth gears, and supports said first and second planet gears so as to relatively rotate;

wherein one of the first sun gear and the first internal tooth gear of the first planetary gear mechanism is non-rotatably fixed, and the other of said first sun gear and said first internal tooth gear is rotated together with one of said aperture controlling rotary plates by a motor, and one of the second sun gear and the second internal tooth gear of the second planetary gear mechanism is driven together with the other of said aperture controlling rotary plates by a phase difference motor.

2. The light source apparatus for an electronic endoscope according to claim 1, wherein said second sun gear and the other of said aperture controlling rotary plates are made integral via a first support member;

wherein said one of said aperture controlling rotary plates is fixed to a second support member which is rotated by the motor;

wherein a rotation-center projection provided on said second support member is relatively rotatably fitted in a support hole formed in said first support member; and wherein an annular support member which is in contact with said support hole and the rotation-center projection is inserted in an annular clearance defined between the support hole and the rotation-center projection.

3. The light source apparatus for an electronic endoscope according to claim 1, wherein said second sun gear and the other of said aperture controlling rotary plates are made integral via a first support member;

wherein said one of said aperture controlling rotary plates is connected to a second support member which is rotated by the motor;

wherein a rotation-center projection provided on said second support member is relatively rotatably fitted in a support hole formed in said first support member;

a plurality of arc-shaped support members, which are in contact with said support hole and a biasing device for biasing each arc-shaped support member toward the support hole, are inserted in an annular clearance defined between said support hole and said rotation-center projection.

4. The light source apparatus for an electronic endoscope according to claim 1, wherein at least one of said first and second planet gears is made of a thermoplastic elastomer and is in the form of a profile shifted gear shifted in a positive direction with respect to a standard gear having the same number of teeth and the same module.

5. The electronic endoscope having a light source apparatus for an electronic endoscope according to claim 1, further comprising:

an operating portion;

an insertion portion extending from said operating portion and inserted into an object to be viewed; and a light guide which is inserted in said operating portion and said insertion portion, said light guide including a distal end extending to a distal end of said insertion portion;

wherein said light source emits illumination light to said light guide.

6. The light source apparatus for an electronic endoscope according to claim 1, said carrier mechanism comprises a pair of carrier plates which are rotatable about an axis coincident with said rotation axis of said rotary shutter, wherein one and the other of said pair of carrier plates supports a pair of said first planet gears and a pair of said second planet gears at both ends thereof, respectively.

7. The light source apparatus for an electronic endoscope according to claim 2, further comprising carrier bearings fitted in center holes formed in said carriers to relatively rotatably support said carriers.

8. The light source apparatus for an electronic endoscope according to claim 1, wherein said first internal tooth gear is fixed so as not to rotate;

wherein said motor drives said first sun gear and said one of said aperture controlling rotary plates; and wherein said phase difference motor drives said second internal tooth gear.

9. The light source apparatus for an electronic endoscope according to claim 8, wherein said second internal tooth gear is rotatably supported by a gear bearing.

10. The light source apparatus for an electronic endoscope according to claim 1, wherein the first sun gear is fixed so as not to rotate;

wherein said first internal tooth gear is secured to said one of said aperture controlling rotary plates and is driven by said motor;

wherein said second internal tooth gear is secured to the other of said aperture controlling rotary plates; and wherein the second sun gear is driven by the phase difference motor.

11. The light source apparatus for an electronic endoscope according to claim 10, wherein one of said first and second internal tooth gears is rotatably supported by a gear bearing.

12. A light source apparatus for an electronic endoscope comprising:

a light source;

a rotary shutter having a rotation axis extending parallel with an optical axis of said light source, for one of intercepting and emitting illumination light emitted from said light source toward a light guide, said rotary shutter being provided with a pair of aperture controlling rotary plates, coaxial with each other, which are selectively capable of rotating one of relative to and together with each other, and which are each provided with light interception portions and opening portions alternately arranged in the rotation direction, wherein a combined opening angle of the opening portions of the rotary shutter is varied by a relative rotation of said pair of aperture controlling rotary plates, and wherein an amount of said light emitted is controlled by integral rotation of said pair of aperture controlling rotary plates;

a first planetary gear mechanism including a first internal tooth gear which is provided coaxial with the rotation axis of said rotary shutter, a first sun gear coaxial with an axis of said first internal tooth gear, and a first planet gear which simultaneously engages with the first internal tooth gear and the first sun gear;

a second planetary gear mechanism including a second internal tooth gear identical to said first internal tooth gear and coaxial with said rotation axis of said rotary shutter, a second sun gear identical to said first sun gear and coaxial with an axis of said second internal tooth gear, and a second planet gear identical to said first planet gear and which simultaneously engages with said second internal tooth gear and said second sun gear; and a carrier mechanism which holds said first and second planet gears in a same phase position, with respect to said first and second internal tooth gears, and supports said first and second planet gears so as to relatively rotate;

wherein said second internal tooth gear is fixed so as not to rotate;

wherein said second sun gear and one of said aperture controlling rotary plates are rotated together;

wherein said first sun gear and the other of said aperture controlling rotary plates are driven by a motor; and wherein the first internal tooth gear is driven by a phase difference motor.

13. The light source apparatus for an electric endoscope according to claim 12, said carrier mechanism comprises a pair of carrier plates which are rotatable about an axis coincident with said rotation axis of said rotary shutter, wherein one and the other of said pair of carrier plates supports a pair of said first planet gears and a pair of said second planet gears at both ends thereof, respectively.

14. The light source apparatus for an electronic endoscope according to claim 12, wherein said first internal tooth gear is rotatably supported by a gear bearing.

* * * * *